(12) United States Patent
Yates

(10) Patent No.: US 7,488,319 B2
(45) Date of Patent: Feb. 10, 2009

(54) RESECTING DEVICE

(76) Inventor: Leroy L. Yates, 4078 - 18th Ave., Bettendorf, IA (US) 52722

( * ) Notice: Subject to any disclaimer, the term of this patent is extended or adjusted under 35 U.S.C. 154(b) by 0 days.

(21) Appl. No.: 11/824,407

(22) Filed: Jun. 29, 2007

(65) Prior Publication Data

US 2008/0009854 A1 Jan. 10, 2008

Related U.S. Application Data

(60) Provisional application No. 60/818,847, filed on Jul. 6, 2006.

(51) Int. Cl.
  *A61B 18/18* (2006.01)
(52) U.S. Cl. .......................... 606/51; 606/41
(58) Field of Classification Search ............ 606/41, 606/44, 49, 113, 51
  See application file for complete search history.

(56) References Cited

U.S. PATENT DOCUMENTS

| | | | |
|---|---|---|---|
| 4,493,320 A | 1/1985 | Treat | |
| 4,655,216 A | 4/1987 | Tischer | |
| 4,917,082 A | 4/1990 | Grossi et al. | |
| 5,290,284 A | 3/1994 | Adair | |
| 5,352,222 A | 10/1994 | Rydell | |
| 5,354,271 A | 10/1994 | Voda | |
| 5,445,638 A | 8/1995 | Rydell et al. | |
| 5,458,598 A | 10/1995 | Feinberg et al. | |
| 5,498,256 A | 3/1996 | Furnish | |
| 5,569,244 A | 10/1996 | Hahnen | |
| 5,582,611 A | 12/1996 | Tsuruta et al. | |
| 5,792,114 A * | 8/1998 | Fiore | 604/171 |
| 5,989,277 A | 11/1999 | LeMaire, III et al. | |
| 6,126,658 A | 10/2000 | Baker | |
| 6,152,923 A | 11/2000 | Ryan | |
| 6,174,309 B1 | 1/2001 | Wrublewski et al. | |
| 6,174,317 B1 | 1/2001 | Engman | |
| 6,176,858 B1 | 1/2001 | Dequesne et al. | |
| 6,190,386 B1 | 2/2001 | Rydell | |
| 6,228,080 B1 | 5/2001 | Gines | |
| 6,322,578 B1 | 11/2001 | Houle et al. | |
| 6,540,737 B2 | 4/2003 | Baher et al. | |
| 6,773,432 B1 | 8/2004 | Clayman et al. | |
| 6,960,210 B2 | 11/2005 | Lands et al. | |
| 7,135,018 B2 | 11/2006 | Ryan et al. | |
| 7,156,846 B2 | 1/2007 | Dycus et al. | |

(Continued)

OTHER PUBLICATIONS

Patton Surigical: www.pattonsurgical.com.

(Continued)

*Primary Examiner*—Roy D Gibson
(74) *Attorney, Agent, or Firm*—Hamilton IP Law, PC; Jay R. Hamilton; Charles A. Damschen

(57) ABSTRACT

A resecting device is disclosed. The resecting device comprises: a handle having a jaw trigger slidably engaged with the handle and mechanically engaged with a spring mechanism communicating a biasing force to the jaw trigger; a fixed shaft portion having a first and a second end, wherein the fixed shaft portion first end is affixed to the housing, wherein the fixed shaft portion second end forms a first jaw member, and wherein the first jaw member has a tissue contact area; and a slidable shaft portion in communication with the spring mechanism and slidable relative to the fixed shaft portion.

38 Claims, 29 Drawing Sheets

U.S. PATENT DOCUMENTS

2006/0064113 A1* 3/2006 Nakao .................. 606/113

OTHER PUBLICATIONS

Tissuelink: www.tissuelink.com.
Ethicon Endo-Surgery: www.ethiconendo.com.
Ligasure Vessel Sealing System: www.ligasure-usa.com.
http://www.devicelink.com/mddi/archive/96/02/013.html.
http://www.devicelink.com/mx/archive/04/01/Varona/html.
http://www.mrg.net/about.cfm?about=news#AP01.
http://www.computermotion.com/productsandsolutions/products/zeus/ZEUSInstruments.cfm.
http://www.remltd.co.uk/forcep_spec.htm.
http://www.everestmedical.com/products-everestmedical.asp?action=productview&ProductID=60.
Koh, Charles H., Total Laparoscopic Hysterectomy Simplified: A New Technique, http://reproductivecenter.com/simplified.html USA.
Koh, Charles H., Total Laparoscopic Hysterectomy Simplified: Speeding The Move To Laparoscopic Hysterectomy. http://reproductivecenter.com/speeding.html USA.
Treat, Michael R., A new Thermal Device for Sealing and Dividing Blood Vessels http://www.starioninstruments.com/PDFs/Treat.pdf USA.
K. Weld and J. Landman, Comparison of cryoablation, radiofrequency ablation and high-intensity . . . , BJU International, vol. 96 Issue 9, p. 1224-1229, Dec. 2005.
Trehan, Ashini K., "Laparoscopic-assisted vaginal hysterectomy: a low complication hysterectomy", Gynaecological Endoscopy, 1997 6, 89-93.
Brolmann et. al., "The laparoscopic Deschamps needle: revival of an old concept"; Gynaecological Endoscopy, 2000 9, 243-247.
Soriano et al., "Recovery from vaginal hysterectomy compared with laparoscopy-assisted vaginal hysterectomy: a prospective . . . ", Acta Obstet Gynecol Scand 80 (2001).

* cited by examiner

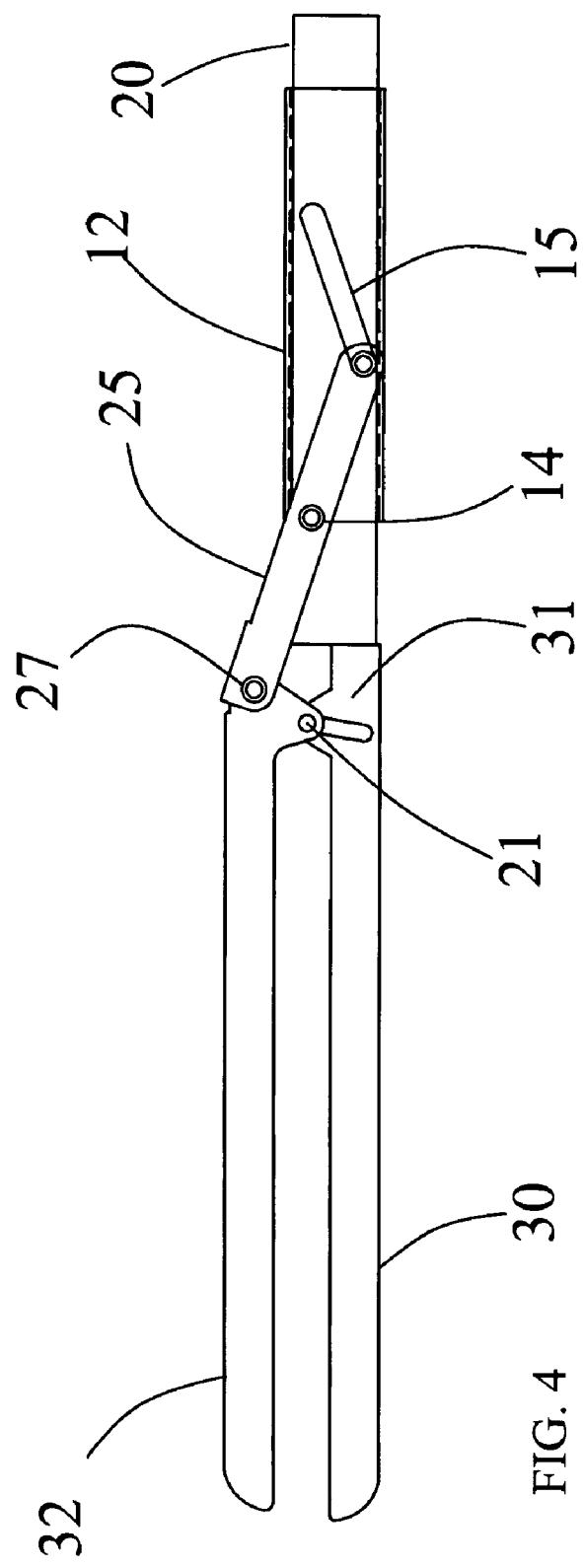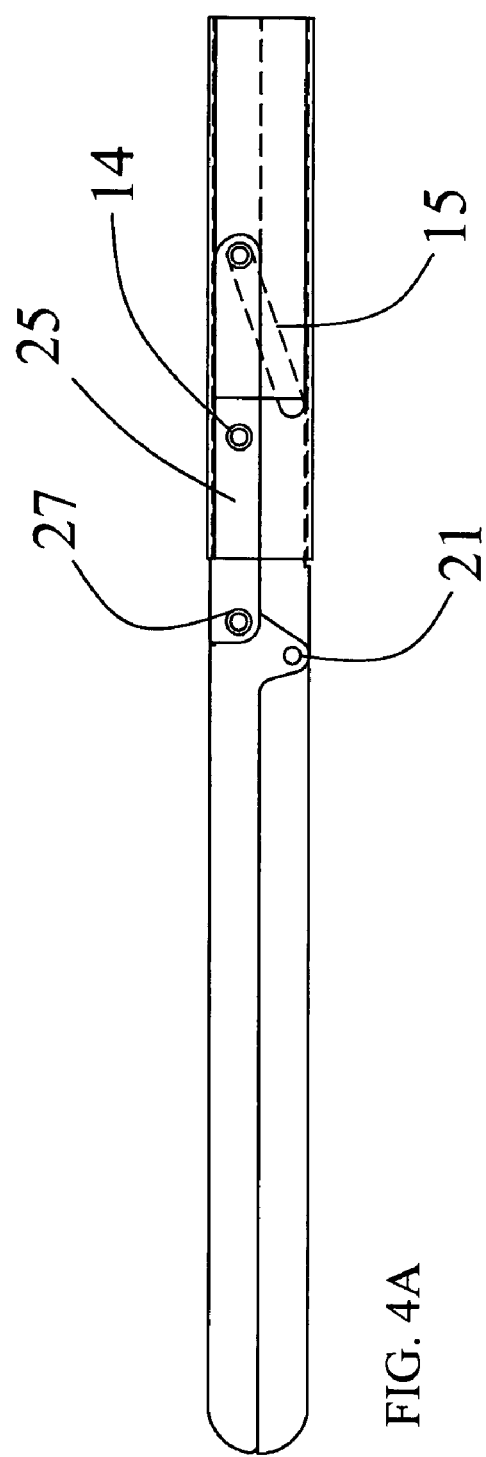
FIG. 4
FIG. 4A

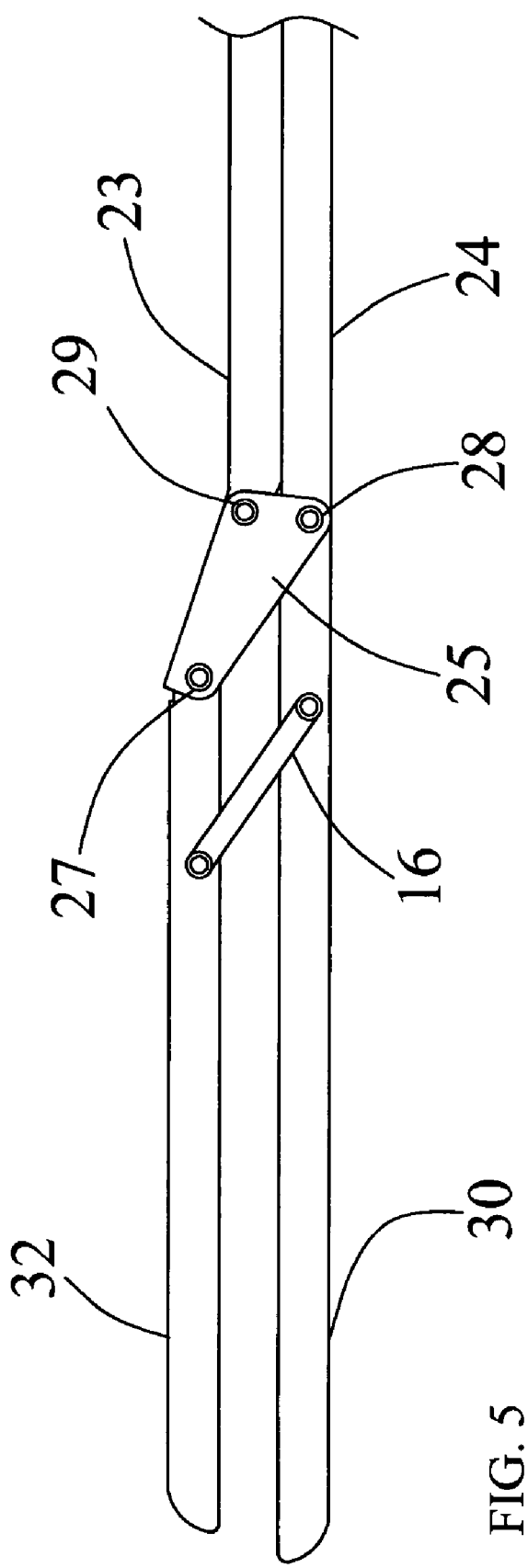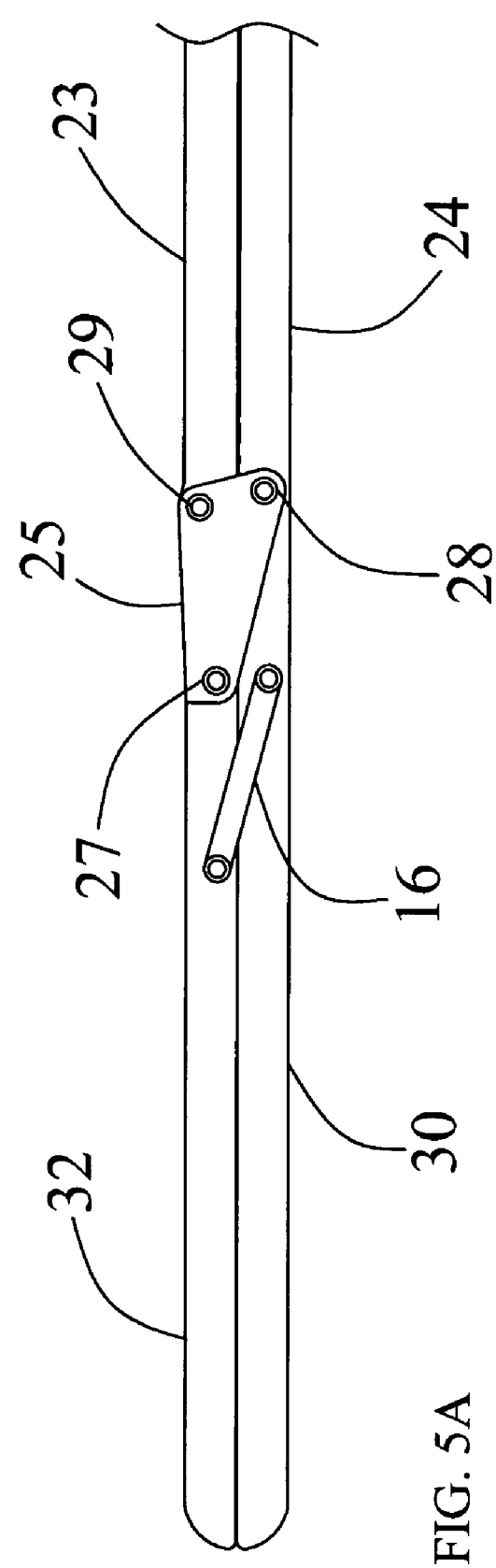
FIG. 5
FIG. 5A

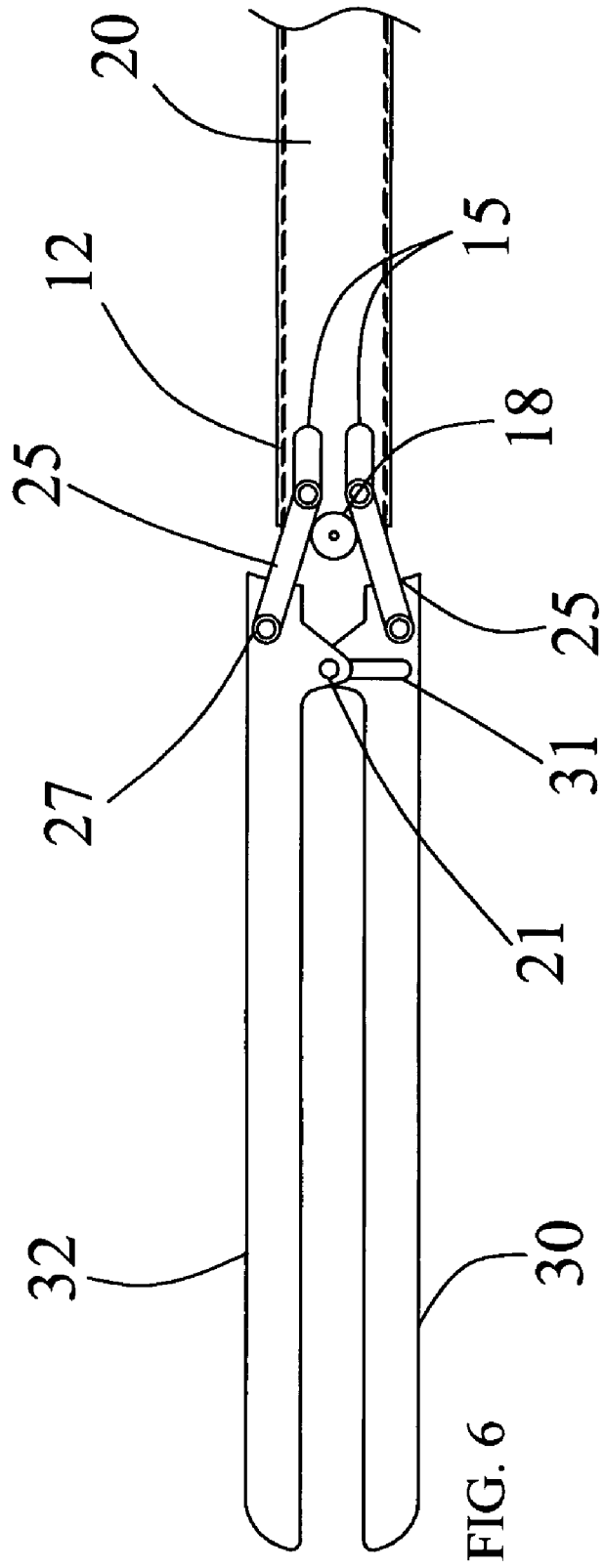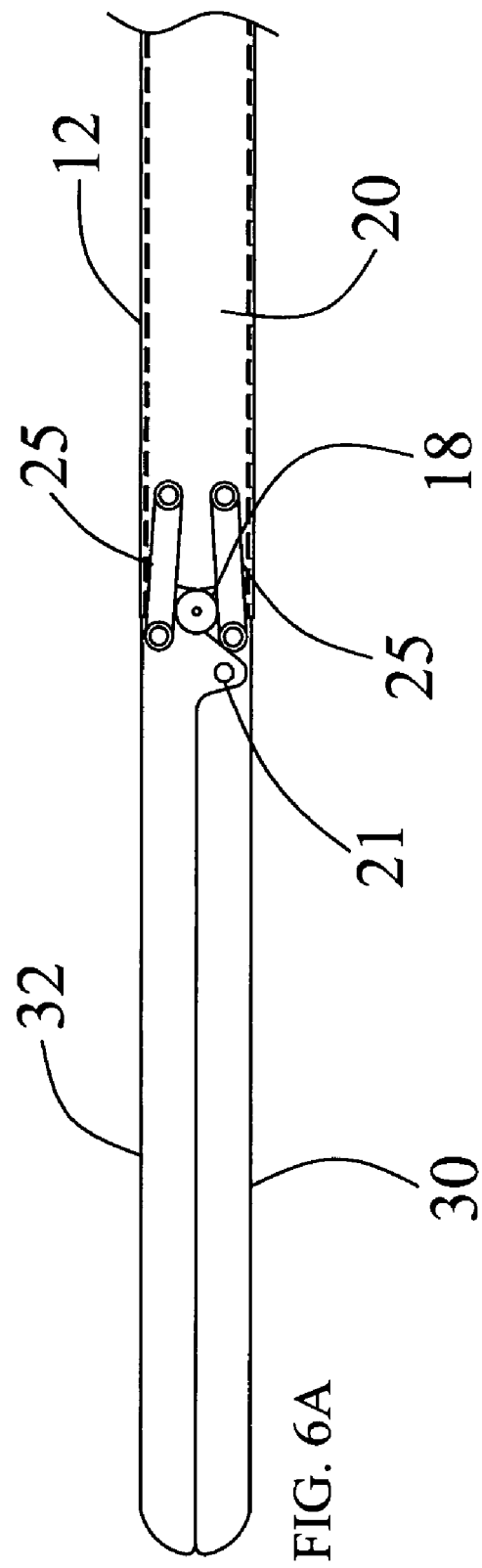
FIG. 6
FIG. 6A

RESECTING DEVICE

CROSS REFERENCE TO RELATED APPLICATIONS

Applicant claims priority under 35 U.S.C. § 119 (e) of provisional U.S. Patent Application Ser. No. 60/818,847 filed on Jul. 6, 2006, which is incorporated by reference herein.

FIELD OF INVENTION

This invention relates to a surgical instrument and, more specifically, to a multi-polar electrosurgical resecting device.

STATEMENT REGARDING FEDERALLY SPONSORED RESEARCH OR DEVELOPMENT

No federal funds were used to develop or create the invention disclosed and described in the patent application.

REFERENCE TO SEQUENCE LISTING, A TABLE, OR A COMPUTER PROGRAM LISTING COMPACT DISK APPENDIX

Not Applicable

AUTHORIZATION PURSUANT TO 37 C.F.R. §§ 1.171 (d), (c)

A portion of the disclosure of this patent document contains material that is subject to copyright and trademark protection. The copyright owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

Each year, approximately 600,000 hysterectomy procedures are performed in the Untied States, totaling more than 5 billion dollars in medical expenses. Many different surgical methods are available for performing a hysterectomy, and the degree of intrusiveness and recovery time are dependent on the surgical method chosen. Typically, for non-endoscopic hysterectomies, the recovery time is approximately six weeks. As technology has progressed, there has been a movement for quicker, safer methods for performing hysterectomies.

Electrosurgical forceps, such as those disclosed in U.S. Pat. No. 7,232,440, utilize both mechanical action and electrosurgical energy to treat tissue. In electrosurgery, electricity alternates current through tissue held between two electrodes. The frequency at which the current alternates should generally be set at 100,000 cycles per second (often referred to as "radio" frequencies) or above. In bipolar electrosurgery, both the positive and ground electrodes are located at the site of surgery (e.g., a forceps wherein one lead is the positive electrode of a circuit and the other lead is the negative electrode of that circuit). In monopolar electrosurgery only the active electrode is in the wound, and the ground electrode is at another location on the patient's body.

The effect of the electrosurgical energy on tissue depends on the waveform of the electrosurgical energy. As is well known to those skilled in the art, the waveform may be manipulated to cut or vaporize tissue, coagulate tissue, or a mixture of both. Tissue dessication occurs when the electrode is in direct contact with the tissue, which may be achieved using several different waveforms.

The CDC has reported a significant increase in the proportion of laparoscopic assisted vaginal hysterectomies (LAVH) over the past decade. In a 1994 study comparing LAVH patients with patients undergoing total abdominal hysterectomies (TAH), it was shown that LAVH patients undergo longer surgical operations and more costly hospital stays, but they also stay in the hospital for significantly less time, have less pain during recovery, and are able to engage in significantly more postoperative activity sooner. Results from a 1997 study comparing patients undergoing LAVH to patients undergoing vaginal hysterectomies showed that although LAVH patients underwent longer, more costly surgery, there was significantly less blood loss associated with the LAVH procedures.

Numerous patents exist for surgical devices designed for endoscopic cholecystectomy; however, there are currently no dedicated devices for endoscopic pelvic surgery. Specifically, U.S. Pat. No. 4,493,320 shows a bipolar electrosurgical cautery snare; U.S. Pat. No. 5,569,244 shows loop electrodes for electrocautery for probes for use with a resectoscope; and U.S. Pat. No. 5,458,598 shows tripolar cutting forceps. The endoscopic cholecystectomy devices now in use are generally very slow, with small cutting/cauterizing areas requiring very high amounts of electricity and high temperatures, which can damage surrounding tissue and result in more time-consuming surgical procedures.

SUMMARY OF THE INVENTION

The present invention consists of an electrosurgical resecting device that is new and different from the prior art. The present resecting device differs from the prior art in that it has both straight jaw and angled jaw embodiments wherein the distance between the jaw members is constant along the length of the jaws. The angular jaw embodiments may be engineered to accommodate a specific pelvic vascular structure corresponding to a specific surgical procedure, and to allow for precise placement of the device inside the abdominal cavity. The present device also differs from the prior art because it provides for rapid treatment of tissue with electrosurgical energy resulting in significantly lower temperatures and requiring lower amounts of energy than the prior art devices. One embodiment of the present device has large tissue contact areas that allow for rapid electrosurgical treatment of tissue. In one embodiment, the tissue contact area is sized to specifically allow for treatment of an entire side of the uterus at once, which is also different from the prior art. Use of the present invention allows total uterine resection in three to five minutes, which is anticipated to be faster than any prior art invention.

Certain embodiments of the resecting device pictured and described herein are exclusively and uniquely designed for a laparoscopic supracervical hysterectomy, total laparoscopic hysterectomy, laparoscopic assisted vaginal hysterectomy, total abdominal hysterectomy, and/or total abdominal supracervical hysterectomy procedure with or without salpingoophorectomy. In these embodiments, the resecting device is used during endoscopic pelvic surgery to rapidly electrosurgically treat the abundant blood supply and the tissue of the infudibulopelvic ligament, proper ovarian ligament, round ligament, fallopian tubes, broad ligament, lateral uterine vessels, and open the vesicouterine fold. The resecting device may also be used to divide the appropriate anatomical structures subsequent to or simultaneously with treatment via electrosurgical energy, and the division of tissue may be aided through treatment of the tissue with electrosurgical energy. These anatomical structures should be electrosurgically treated and divided in thirty to sixty seconds per side and the cervix should be hemostatically amputated within two to three seconds, when necessary according to the specific procedure. Utilizing the resecting device alone it is anticipated to be the fastest uterine resector of any prior art (three to five minutes). In other embodiments, the resecting device is used for other types of endoscopic or laparoscopic surgery, such as a nephrectomy or splenectomy. Other alternative embodiments may be used with open surgical procedures. Accordingly, the scope of the present invention is not limited by the specific method of use of the resecting device or the surgical procedure for which a specific embodiment of the resecting device is designed.

DETAILED DESCRIPTION—BRIEF DESCRIPTION OF THE DRAWINGS

FIG. 4 is a detailed view of a second embodiment of the jaw members in an open position.

FIG. 4A is a detailed view of the second embodiment of the jaw members in a closed position.

FIG. 5 is a detailed view of a third embodiment of the jaw members in an open position.

FIG. 5A is a detailed view of the third embodiment of the jaw members in a closed position.

FIG. 6 is a detailed view of a fourth embodiment of the jaw members in an open position.

FIG. 6A is a detailed view of the fourth embodiment of the jaw members in a closed position.

DETAILED DESCRIPTION OF THE INVENTION

1. General Method of Use of the Invention

A method of use for one embodiment of the resecting device is explained herein, which method explicitly refers to various anatomical structures and procedures undertaken during a hysterectomy. The method of use may differ depending on the specific embodiment of the resecting device and/or the specific procedure undertaken. Throughout this application, "treatment of tissue by electrosurgical energy" or any variation thereof is meant to include cauterization, solidification, coagulation, dessication, division, sealing, or any other effect on tissue achieved through application of electrosurgical energy to the tissue. Accordingly, the effect of the application of electrosurgical energy to tissue will vary from one procedure or use of the resecting device to the next, and such effect is not intended to limit the present invention or the type of electrosurgical energy that may be used therewith.

Step 1. For the specific procedure explained herein, after the periumbilical laparoscope and two operating trocars are placed in the right and left lower abdominal quadrants, one trocar is removed and replaced by a specialized trocar outfitted with the introducer sheath assembly (see FIGS. 12A-12D).

Step 2. The trocar button on the specialized trocar is depressed to cause the stylus to pierce the distal end of the introducer sheath and the trocar is removed from the introducer sheath. The resecting device is then inserted into the sheath (FIG. 12G). Since the jaw members of the resecting device in this embodiment are designed with a curve, the flexibility of the introducer sheath allows placement of the resecting device into the abdominal cavity without straying into subcutaneous, preperitoneal, or rectus muscle compartments. The specialized trocar and introducer sheath are particularly useful for use with obese patients because the abdominal wall of obese patients may be considerably thicker than the abdominal wall of non-obese patients. Once the resecting device is positioned in the abdomen, the introducer sheath may be pulled up and away from the shaft of the resecting device and discarded (see FIG. 13).

Figure 15:
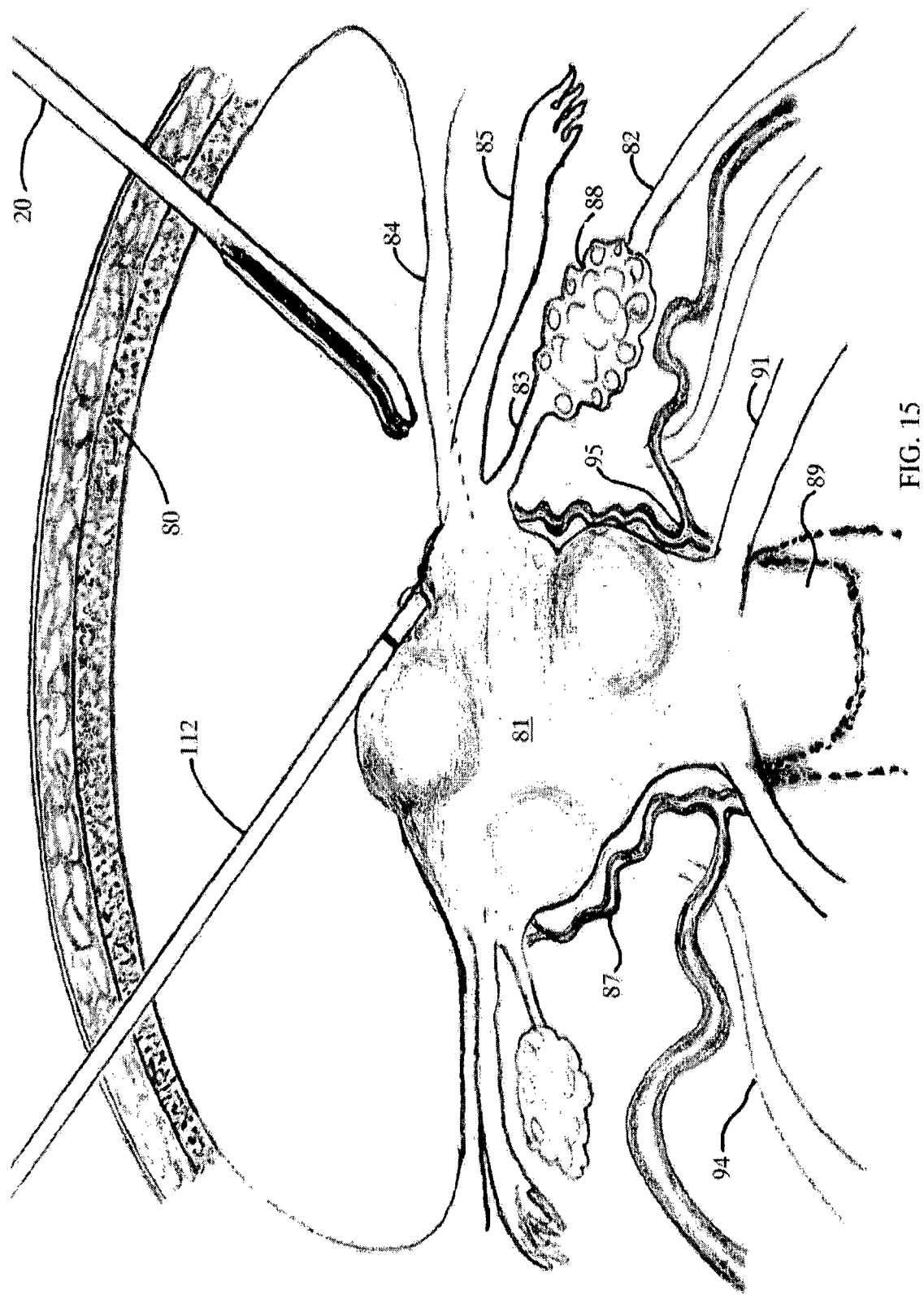
FIG. 15 is another detailed view of one embodiment of the resecting device positioned within a human abdomen.
Figure 16:
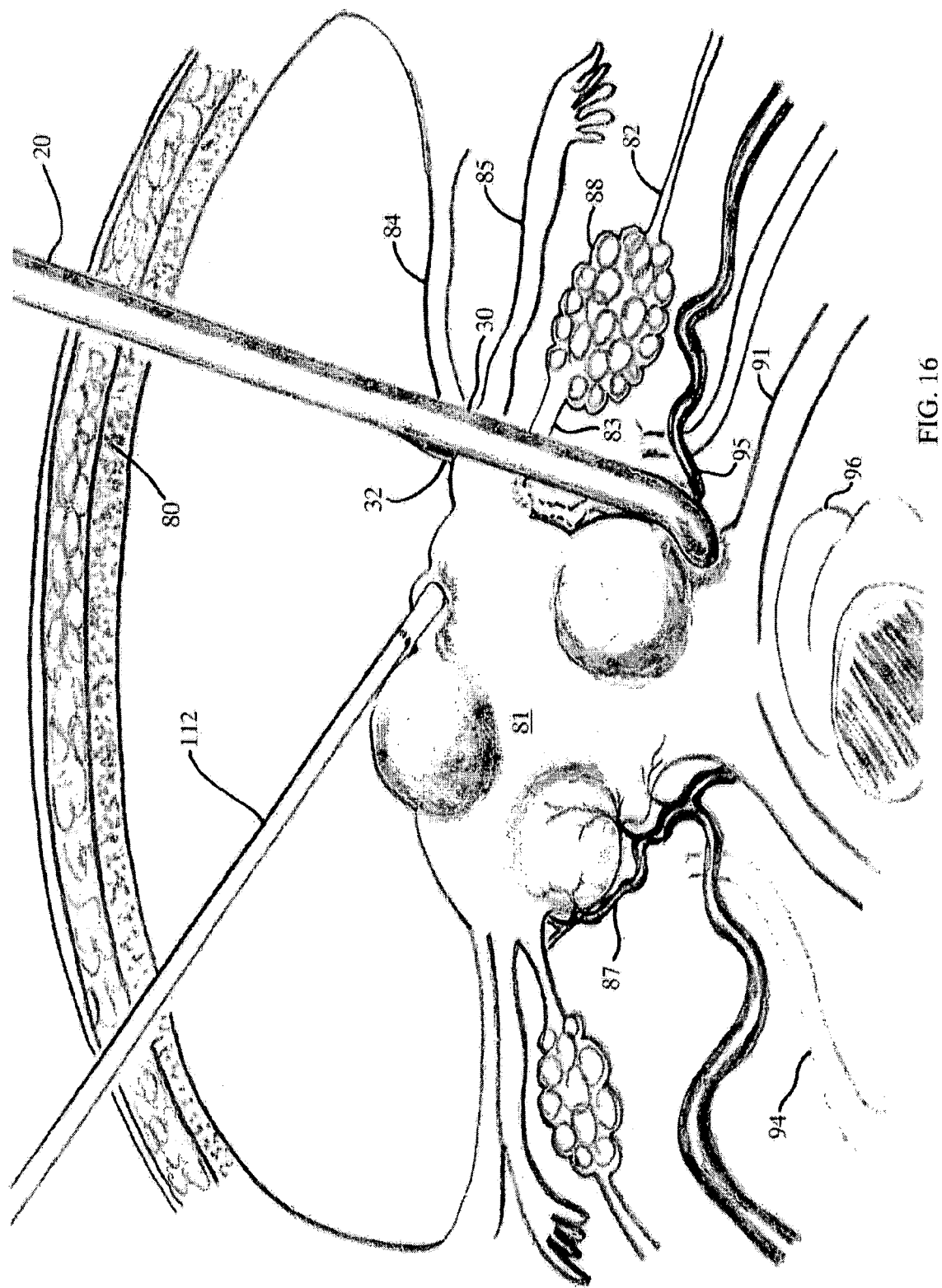
FIG. 16 is a detailed view of one embodiment of the resecting device with the jaw members engaging the tissue on one side of a human uterus.
Figure 18:
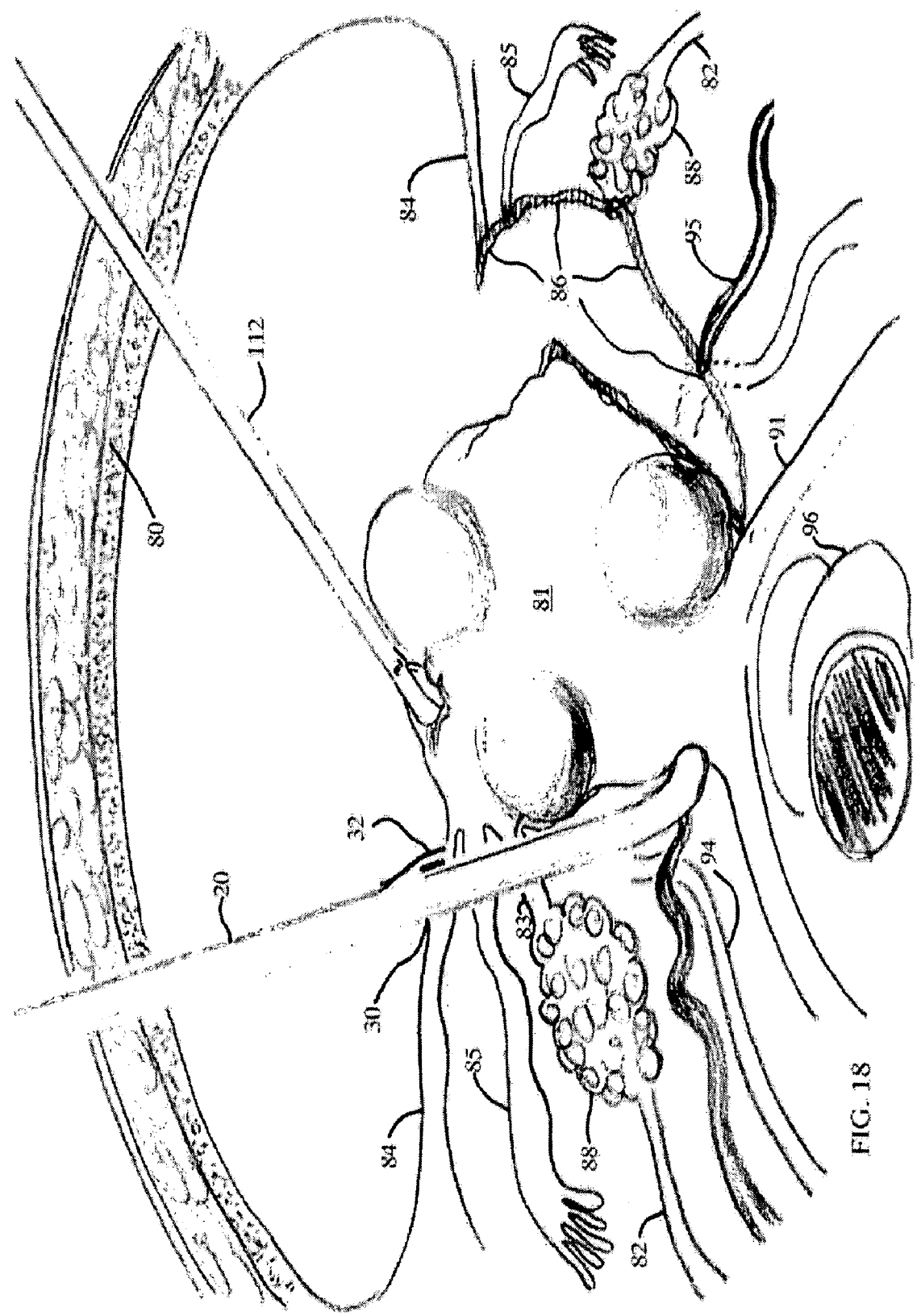
FIG. 18 is a detailed view of one embodiment of the resecting device with the jaw members engaging the tissue on the contra-lateral side of a human uterus.

Step 3. The jaw members are allowed to open (FIG. 15), as in the normal state of the resecting device. The resecting device is positioned over the pelvic anatomy to be electrosurgically treated and the user squeezes the jaw trigger so that the anatomy to be electrosurgically treated comes into contact with the tissue contact areas of the jaw members (FIGS. 16 and 18). If the resecting device is outfitted with a jaw trigger lock, the lock may be engaged at this time. The user presses the jaw energizing button of the electrode selector so that the electrode selector directs electrosurgical energy to the heavy metal contacts in the jaw members. The foot pedal is depressed to activate the electrosurgical energy to electrosurgically treat the tissue held between the jaw members.

Step 4. The user presses the blade energizing button of the electrode selector to select the bipolar blade (which utilizes the jaw member electrodes as the ground contact). The blade is advanced while activating the foot switch to electrosurgically treat blood vessels and tissues as it divides them. The handle of the resecting device is rotated 180 degrees so that the jaw members now follow the periphery of the opposite side of the pelvic structure (FIG. 18) and steps 1-4 are performed on the contralateral tissues. In a hysterectomy, the curved jaw members will allow the user easy access to the pelvic tissues immediately adjacent to the uterocervical junction at the level of the vesicouterine fold.

Figure 19:
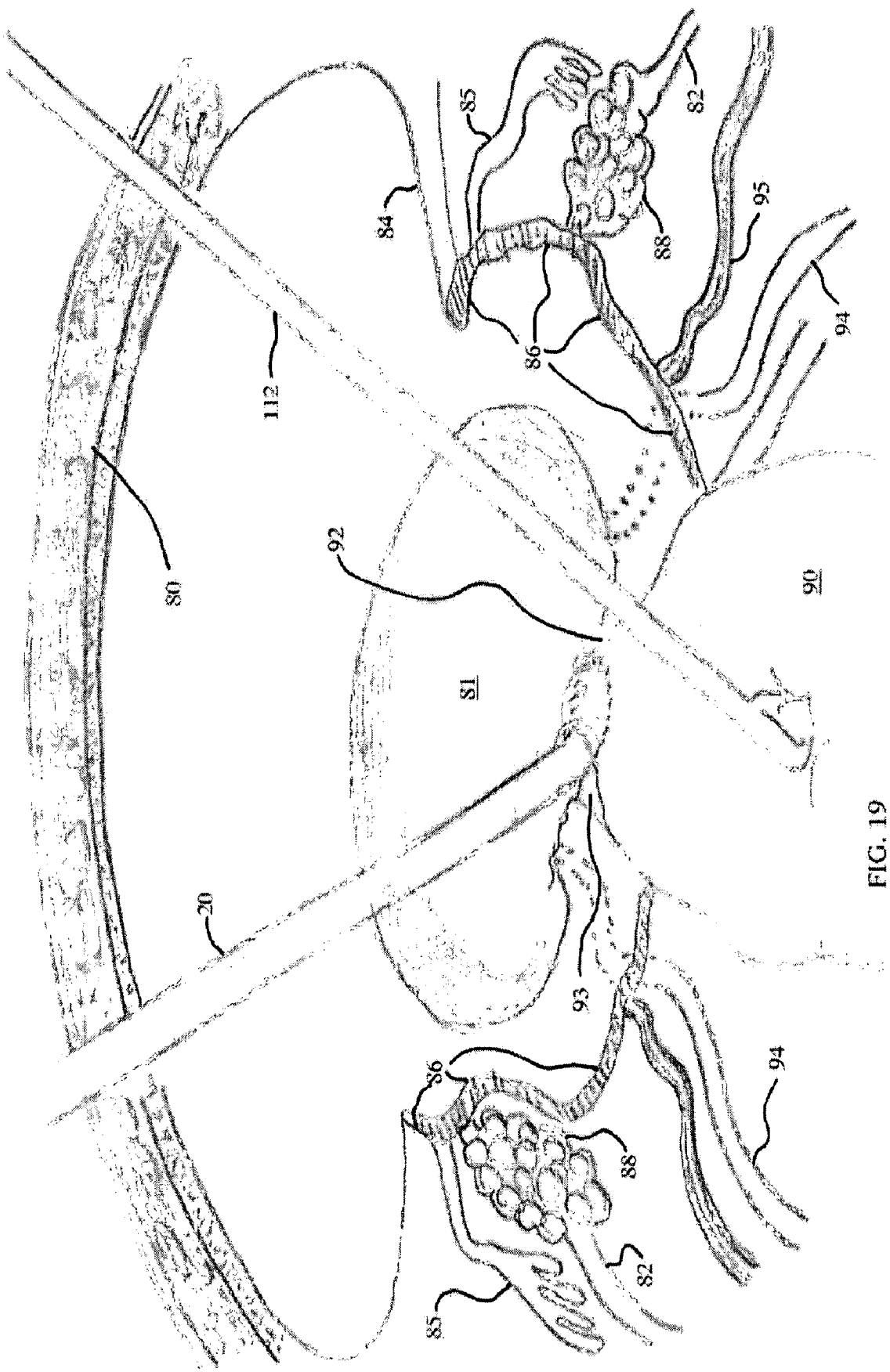
FIG. 19 is a detailed view of one embodiment of the resecting device with the jaw members engaging the anterior vesicouterine fold of a human uterus.

Step 5. The anterior vesicouterine fold is undermined and clamped with the jaw members (FIG. 19). The jaw energizing button is again selected, the foot switch is activated, and the tissue is electrosurgically treated. At this point, the jaw energizing button may be selected to utilize electrosurgical energy blade routed to the blade. The vesicouterine fold tissue is divided by the user's actuating the blade, dividing the tissue held between the jaw members. The jaw members may be used to bluntly dissect the bladder from the lower uterine segment.

Figure 20:
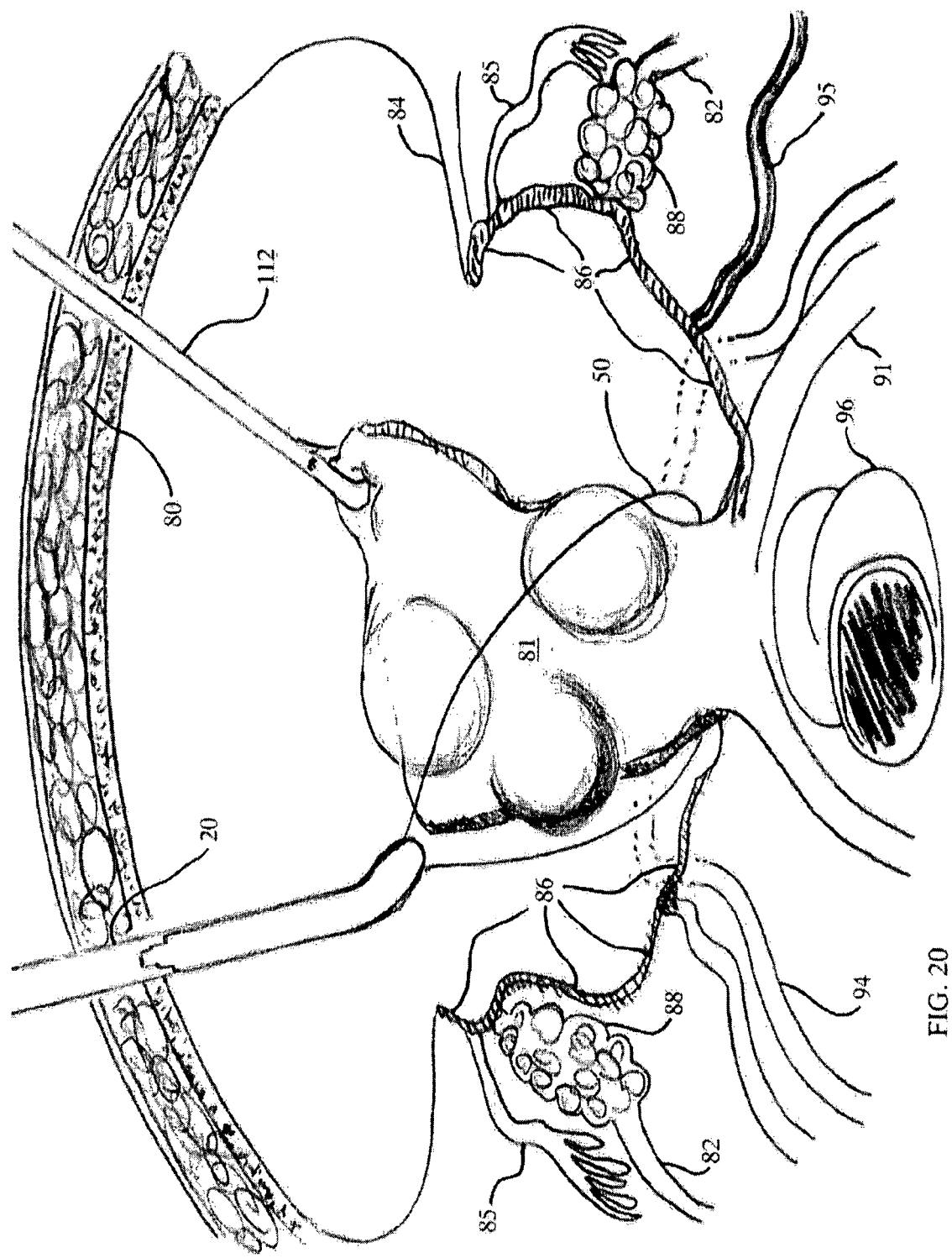
FIG. 20 is a detailed view of one embodiment of the resecting device with the wire loop deployed over a human uterus having both sides divided.
Figure 21:
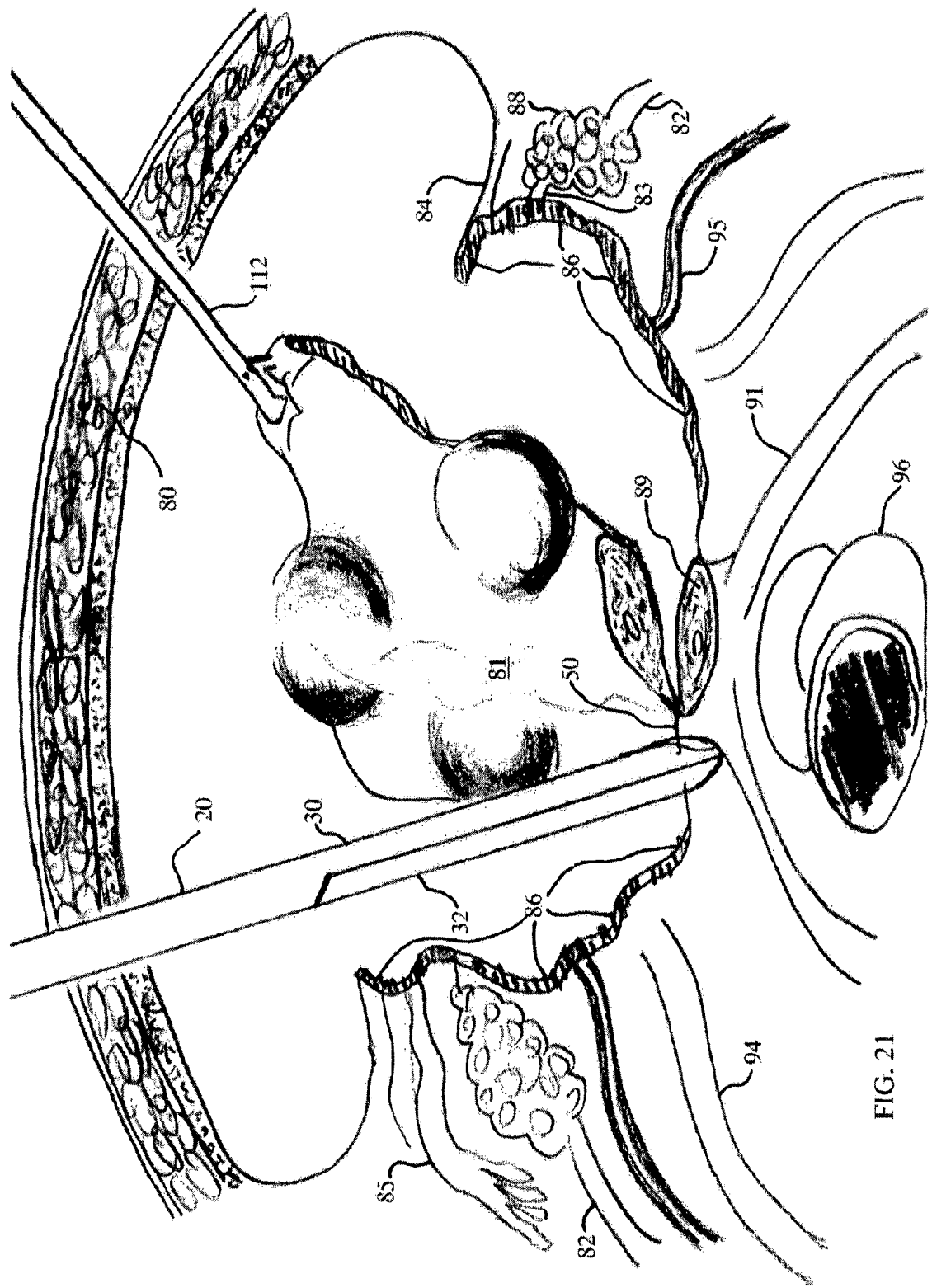
FIG. 21 is a detailed view of one embodiment of the resecting device with the wire loop being retracted to divide the uterocervical junction.

Step 6. The wire loop switch is positioned so that the electric motor rotates the wire spool in a direction to deploy the wire loop. The wire loop is placed over the top of the uterus and positioned proximal the cervix near the uterocervical junction (FIG. 20). The wire loop energizing button on the resecting device is selected so that the electrode selector opens the circuit from the source of electrosurgical energy to the wire loop. The wire loop switch is positioned so that the electric motor rotates the wire spool in a direction to retract the wire loop. When the wire is tight against the cervix the foot switch is activated, energizing the wire loop with electrosurgical energy. The wire loop and contact plate on the distal end of the resecting device shaft complete the circuit causing the loop wire to electrosurgically treat the tissue at the uterocervical junction in contact with the wire loop. At this point, the wire loop may be retracted further to divide the tissue in contact with the wire loop (FIG. 21).

Step 7. The resected pelvic structures are removed using a morcellator. The abdomen is deflated, the instruments are removed, the incisions are closed, and wound dressings are placed.

2. Device Features

After analyzing the weaknesses of each prior art surgical device, especially those used in laparoscopic or endoscopic procedures, there are several major features of this resecting device that will dramatically decrease surgical operating time, improve safety and consistency, and increase convenience.

In one embodiment, the jaw application site is curved to accommodate the specific pelvic vascular architecture according to the procedure to be performed (FIGS. 8A-D). Specifically, the jaw members may be angled to emulate the outer curvature of a human uterus. The cantilevered jaw member arrangement allows for more tissue to be held between the jaw members without the need to increase vertical clearance at the distal ends of the jaw members (i.e., there is no scissoring effect).

Teflon-coated, heavy metal contacts may be fused to a rigid, heat-stable polymer body to form tissue contact areas for delivering electrosurgical energy to tissue. This also allows the jaw members to resist heat deformation and allow the user to apply pressure during electrosurgical tissue treatment. Additionally, the jaw members may be up to sixteen centimeters long, and therefore provide the largest endoscopic electrosurgical energy delivery surface available; which allows for an extremely rapid cutting speed with precise anatomic placement (FIGS. 16 and 18). The Teflon coating prevents electrosurgically treated tissue from sticking to the tissue contact areas following energizing of the jaw members. A semiconductor chip may be used to alternate the electrosurgical energy between the tissue contact areas on the first and second jaw members; which facilitates cooling of tissues to limit lateral thermal damage and enhance electrosurgical treatment.

The unique electrode selector, which prevents electrosurgical energy flow to any electrode other than that selected by the user, adds safety by avoiding inadvertent energy discharge from an electrode other than the one desired by the user. As shown in FIGS. 16 and 18, one entire side of the uterus is treated at once in most cases.

In one embodiment, an insulated rod is soldered onto the unique blade assembly (in the embodiments pictured herein, a blade assembly is not used). An electrical conduit attaches to the blade and/or blade assembly within the handle to provide a conduit for electrosurgical energy. As the blade travels forward along the blade track, the electrode selector may be positioned so that bipolar electrosurgical energy treats tissue in contact with the blade.

The handle of the resecting device, which is ambidextrous, may be rotated 180 degrees to effectively treat both sides of pelvic structures and to facilitate easy deployment of the wire loop. The unique wire loop (if present for that particular embodiment) may be deployed by moving the wire loop switch to the appropriate position. A motorized spool unwinds the wire loop, which is especially convenient for hysterectomy procedures because the wire loop may be deployed over the uterus. Once the loop drapes over the uterus, the user may move the wire loop switch to the appropriate position to cause the electric motor to reverse, thereby reversing the wire spool and retracting the wire loop tightly against the cervix (FIG. 21). The electrode selector is positioned to allow electrosurgical energy to pass to the wire loop; which electrosurgically treats the tissue in contact with the wire loop. Retracting the wire loop while simultaneously energizing the wire loop may be used to hemostatically amputate the cervix in two to three seconds. The uterus is now completely disconnected and ready for endoscopic removal using an endoscopic morcellator (see Gynecare Morcellator). In alternative embodiment, the wire spool includes a wire spool handle so that the user may manually retract and deploy the wire loop.

Radiofrequency (Rf) energy lowers the thermal energy delivered to the tissue, decreasing excess lateral thermal damage. Usual electrosurgical devices achieve temperatures of several hundred degrees (up to 800 degrees C.) and operate in the 150 to 300 watt range at up to 800 volts. The present resecting device is capable of operating in an Rf capacity in the 10-15 watt range with 80 volts to minimize lateral excess thermal tissue damage.

3. General Description of an Exemplary Embodiment

| ELEMENT DESCRIPTION | ELEMENT # |
| --- | --- |
| Resecting Device | 10 |
| Shaft Sheath | 11 |
| Slidable Sleeve | 12 |
| Translator Connector | 13 |
| Shaft/Link Connector | 14 |
| Link Groove | 15 |
| Second Link | 16 |
| Separator | 18 |
| Shaft | 20 |
| Knob | 21 |
| Handle | 22 |
| Slidable Shaft Portion | 23 |
| Fixed Shaft Portion | 24 |
| Link | 25 |
| Pin | 26 |
| Second Jaw Member/Link Connector | 27 |
| Fixed Shaft Portion/Link Connector | 28 |
| Slidable Shaft Portion/Link Connector | 29 |
| First Jaw Member | 30 |
| Slot | 31 |
| Second Jaw Member | 32 |
| Tissue Contact Area | 34 |
| Pin Aperture | 36 |
| Pin Cap | 38 |
| Blade | 40 |
| Blade Track | 42 |
| Electrical Conduit | 44 |
| Blade Actuator | 46 |
| Wire Loop | 50 |
| Electric Motor | 51 |
| Contact Plate | 52 |
| Wire Spool | 53 |
| Wire Loop Switch | 54 |
| Wire Aperture | 56 |
| Wire Loop Handle | 58 |
| Insulated Conduit | 59 |
| Spring Mechanism | 60 |
| Electrode Selector | 62 |
| Foot Pedal | 64 |
| Jaw Button | 66 |
| Blade Button | 67 |
| Loop Button | 68 |
| Jaw Trigger | 70 |
| Jaw Trigger Beam Engager | 74 |
| Beam | 76 |
| Translator | 78 |
| Abdominal Wall | 80 |
| Uterus | 81 |
| Infundibulopelvic Ligament | 82 |
| Proper Ovarian Ligament | 83 |
| Round Ligament | 84 |
| Fallopian Tube | 85 |
| Broad Ligament | 86 |
| Lateral Uterine Vessel | 87 |
| Ovary | 88 |
| Cervix | 89 |
| Bladder | 90 |
| Uterosacral Ligament | 91 |
| Anterior Vesicouterine Fold | 92 |
| Uterocervical Junction | 93 |
| Ureter | 94 |
| Uterine Artery | 95 |
| Rectum | 96 |
| Introducer Sheath | 100 |
| Trocar | 101 |
| Trocar Button | 102 |
| Stylus | 104 |
| Perforation | 106 |
| Introducer Sheath Ring | 108 |
| Introducer Sheath Body | 110 |
| Grasping Forcep | 112 |

Referring now to the figures, a multi-polar electrosurgical resecting device 10 is shown. The resecting device 10 is designed for use in surgical procedures, with specific embodiments pictured herein designed for laparoscopic supracervical hysterectomies, total laparoscopic hysterectomies, laparoscopic assisted vaginal hysterectomies, total abdominal hysterectomies, and/or total abdominal supracervical hysterectomies with or without salpingoophorectomy. However, the resecting device 10 may also be used in open surgery or other types of endoscopic or laparoscopic surgery, such as nephrectomies or splenectomies, among others. In the embodiment shown in FIG. 1, the resecting device 10 is comprised of a shaft 20 affixed to a handle 22 having a jaw trigger 70. The jaw trigger 70 works in conjunction with a spring mechanism 60, shown in FIGS. 2 and 2A, to manipulate the position of the second jaw member 32 relative to the first jaw member 30. In cooperation, the jaw members 30, 32 may be used to grip tissue. The resecting device 10 may be fashioned with a spring loaded jaw trigger lock (not shown) to lock the position of the jaw trigger 70, and thereby lock the position of the jaw members 30, 32 relative to one another. Also mounted to the handle 22 in this embodiment is a multi-position electrode selector 62. The handle 22 may be constructed of any material suitable for the particular application, which material is known to those skilled in the art, such as high-density polyethylene, aluminum, polyester, or other suitable material. In an embodiment not pictured herein, the handle 22 is composed of a material that is transparent or semi-transparent, and an illumination source is positioned within the handle 22 to illuminate the handle 22 for ease of use. Alternatively, the handle 22 could be made of a material already disclosed in prior art that glows after exposure to light. The arrangement of the handle 22 comprises one type of handle means as recited in the claims.

In the exemplary embodiment, the handle 22 is fashioned as two pieces of approximately equal width. Various elements within the handle 22 may be hermetically sealed in any specific embodiment. For example, if the resecting device 10 is equipped with a motorized wire spool 53, an electrode selector 62 and associated buttons, and/or an internal light (not shown) for illuminating the handle 22 and/or buttons 66, 67, 68, the handle 22 may be fashioned so that each element is hermitically and electronically shielded from other elements as well as the environment external to the handle 22. That is, the portion of the handle 22 that houses the electric motor 51 may be fashioned so that the electric motor 51 is sealed from air, water, and/or electronic interference from other portions of the resecting device 10 and/or other such elements external to the resecting device 10. Any portion of the handle 22 may be fashioned to provide similar sealing for the element or elements arranged within that portion of the handle 22, and the elements of the resecting device 10 that are positioned within a sealed portion of the handle 22 will vary depending on the specific embodiment.

The shaft 20 and a portion of the handle 22 in the exemplary embodiment shown in FIGS. 1, 1A, 2, 2A, 7, 7A, 9, 10, 10A, and 10B encloses the bipolar cutting blade 40 and the bipolar wire loop 50 when the wire loop 50 and blade 40 are in the retracted positions. The shaft 20 of the resecting device 10 may be comprised of a heat stable polymer or other suitable material known to those skilled in the art, such as aluminum, metal, or an alloy thereof. Alternatively, the shaft 20 could be formed of a plurality of materials. It may also be formed in different configurations rather than as one single piece. For example, the shaft 20 could be formed of an interior material that provides thermal and electrical insulation positioned within a shell made of a different material. In the exemplary embodiment, the shaft 20 is formed of two portions; a slidable shaft portion 23 and a fixed shaft portion 24. The slidable shaft portion 23 slides in the axial direction relative to the fixed shaft portion 24. The second jaw member 32 is attached to the slidable shaft portion 23, which facilitates actuation of the second jaw member 32 in this embodiment. In the embodiment shown in FIGS. 1, 1A, 2, 2A, and 10, an axial portion of the shaft 20 is enclosed in a shaft sheath 11 radially encompassing a portion of both the slidable shaft portion 23 and fixed shaft portion 24 to prevent the slidable shaft portion 23 or the fixed shaft portion 24 from buckling when the jaw trigger 70 is actuated. Jaw members 30 and 32 are one type of gripping means as recited in the claims.

Figure 2:
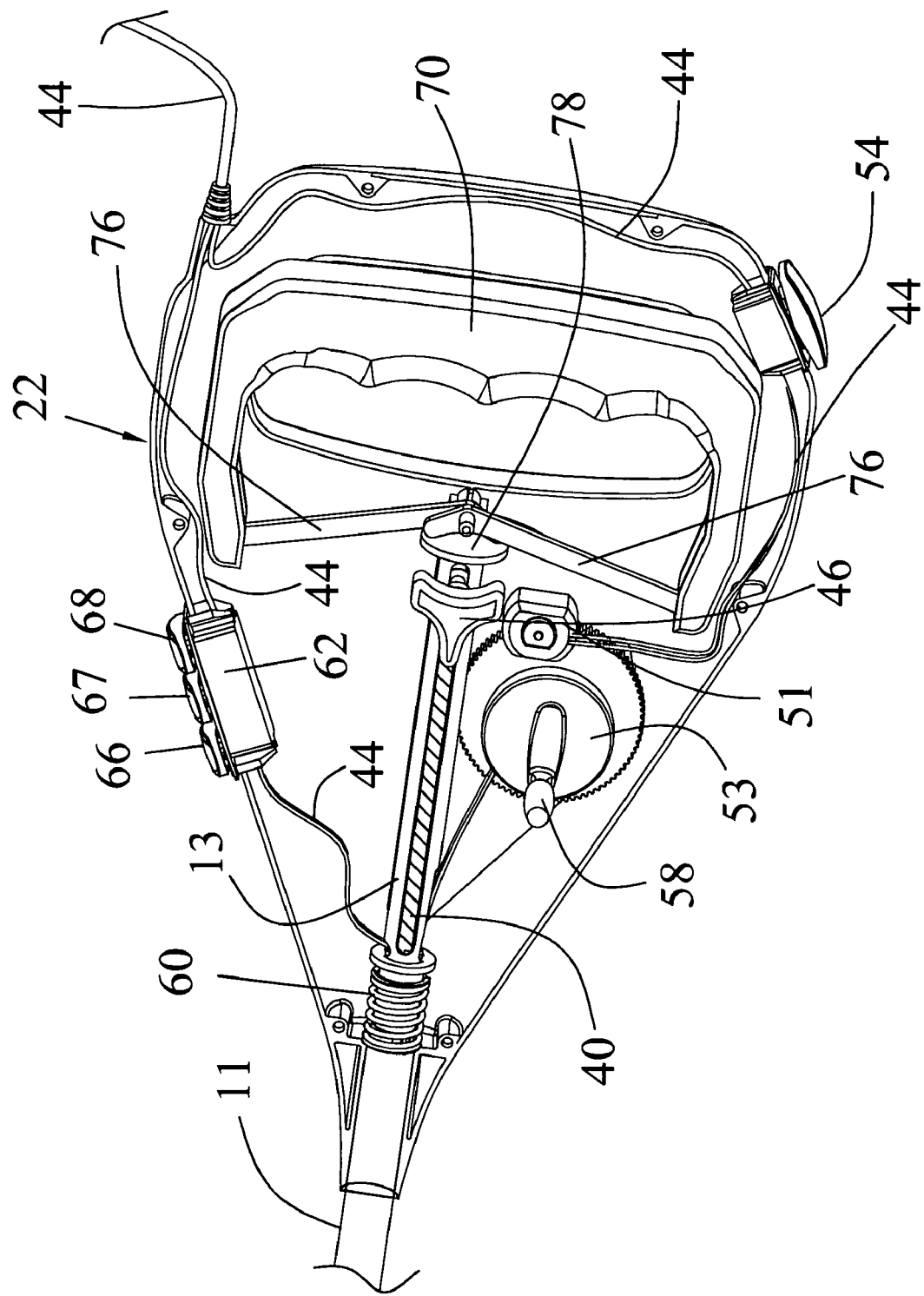
FIG. 2 is a detailed view of the internal portions of the handle of the first embodiment.
Figure 2A:
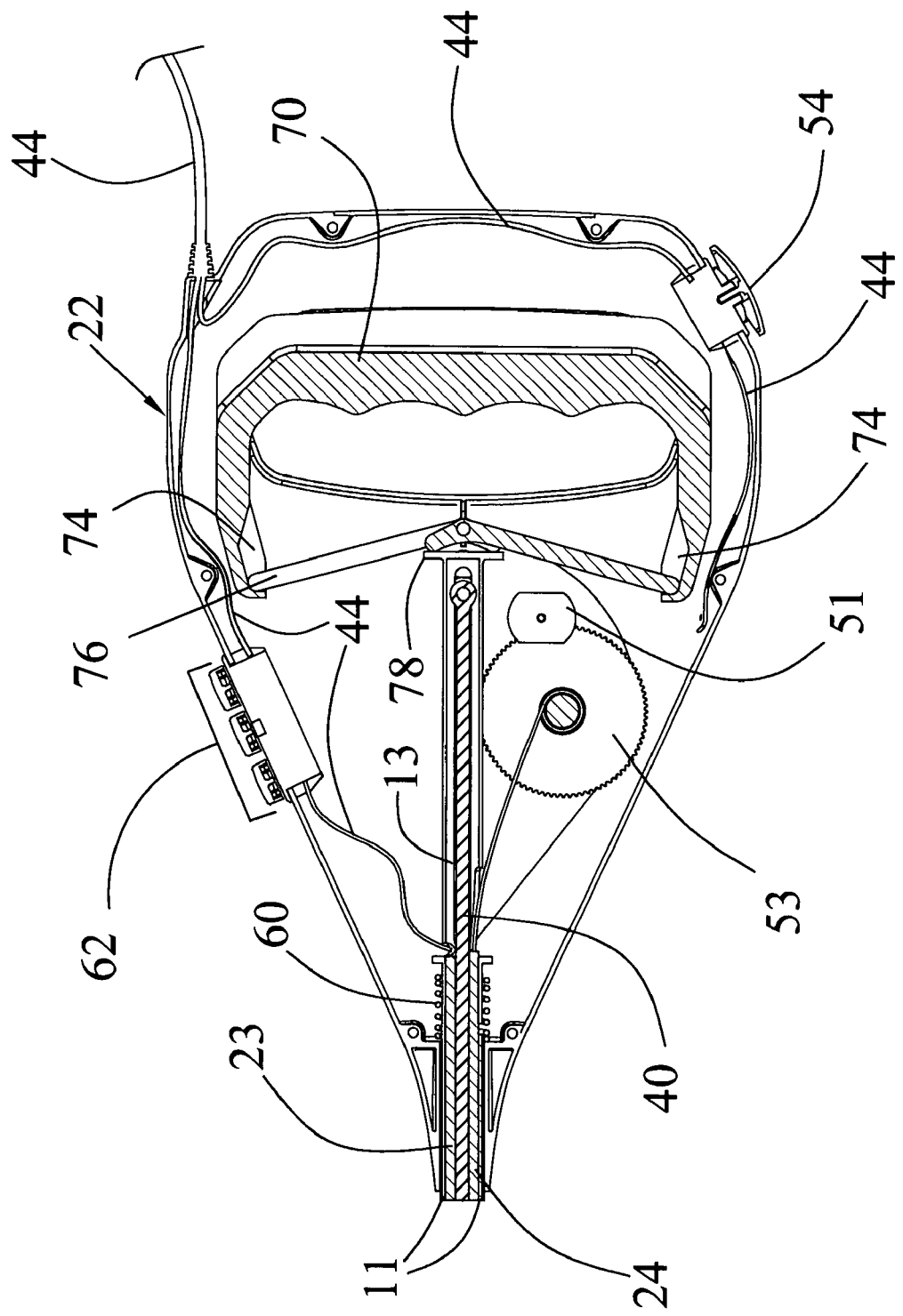
FIG. 2A is a detailed, cutaway view of the handle of the first embodiment.

A detailed view of one embodiment of the internal elements of the handle 22 showing the jaw trigger 70 and the spring mechanism 60 is shown in FIG. 2. A cross-sectional view of the same embodiment of the handle 22 is shown in FIG. 2A. The handle 22 in the exemplary embodiment is designed so that the resecting device 10 may be used by either the right or left hand of the user without need to adjust the resecting device 10. Other shapes and embodiments of the handle 22 will be obvious to those skilled in the art, and variations to the embodiments described and disclosed herein will occur without departure from the spirit and scope of the present invention. As the handle 22 is squeezed, the jaw trigger 70 moves away from the shaft 20 in an axial direction with respect to the shaft 20, and the jaw trigger beam engagers 74, which communicate to the beams 76 mechanical forces imparted to the jaw trigger 70, move in that same direction. This causes the beams 76, which are pivotally engaged to one another, to impart a force to the translator 78, which is mechanically engaged with the slidable shaft portion 23 through the translator connector 13. In this embodiment, the translator 78 is fashioned as a disk oriented so that the shaft 20 and the disk share a similar axis. The translator 78 is connected to the slidable shaft portion 23 through the translator connector 13, so that the slidable shaft portion 23, translator 78, and translator connector 13 may be formed as one piece. The spring mechanism 60 biases the translator 78 in an axial direction away from the shaft 20, which biases the slidable shaft portion 23 in the same direction, thereby separating the jaw members 30, 32 unless an external force is applied to the jaw trigger 70. As the handle 22 is squeezed by the user and the jaw trigger 70 depressed, the beams 76 cause the translator 78 to work against the force of the spring mechanism 60, and when the force imparted from the beams 76 to the translator 78 overcomes the spring force of the spring mechanism 60, the translator 78 will cause the slidable shaft portion 23 to slide relative to the fixed shaft portion 24 in an axial direction away from the handle 22, subsequently causing the second jaw member 32 to move towards the first jaw member 30.

Figure 1:
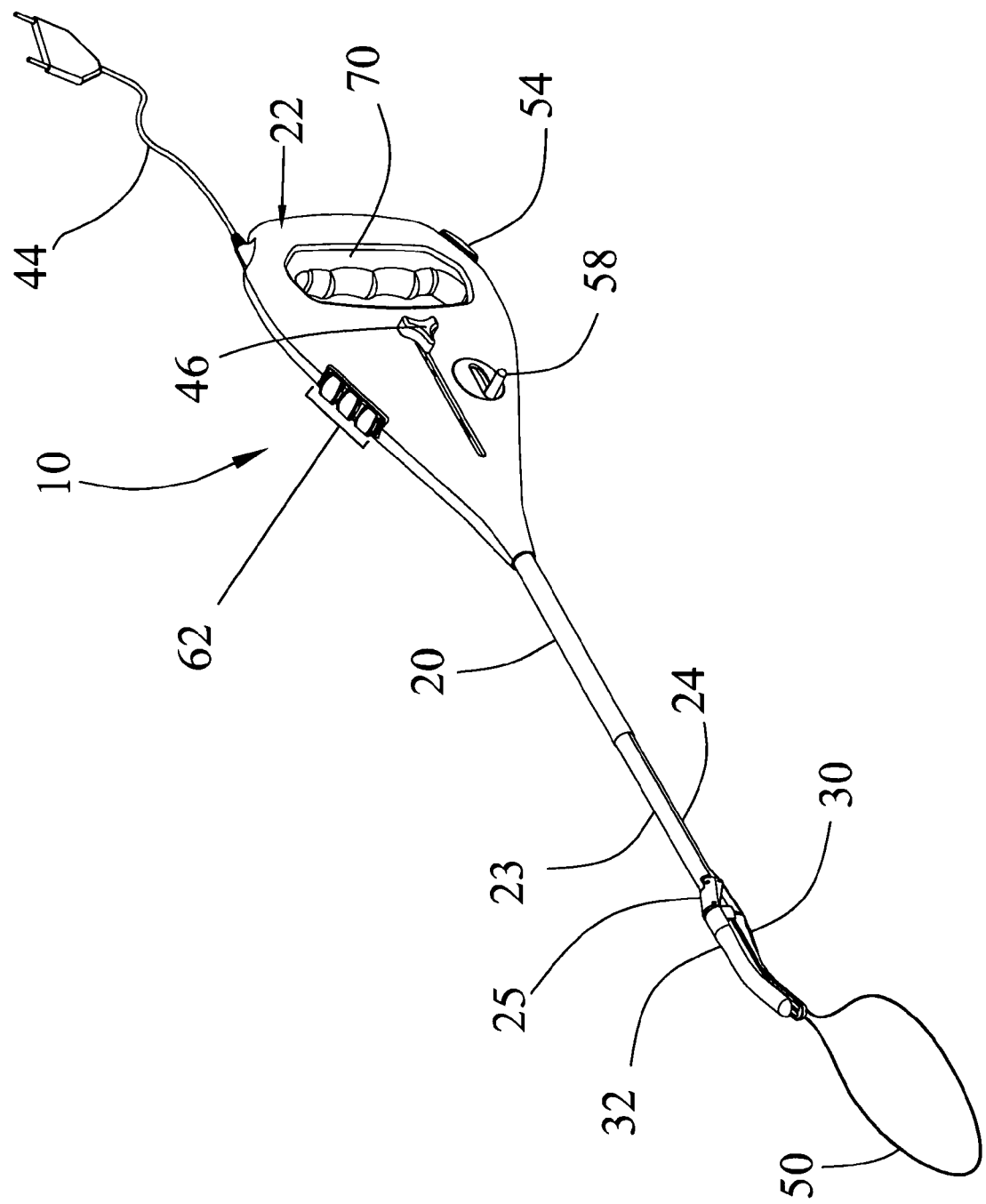
FIG. 1 is a perspective view of a first embodiment of the present invention.
Figure 1A:
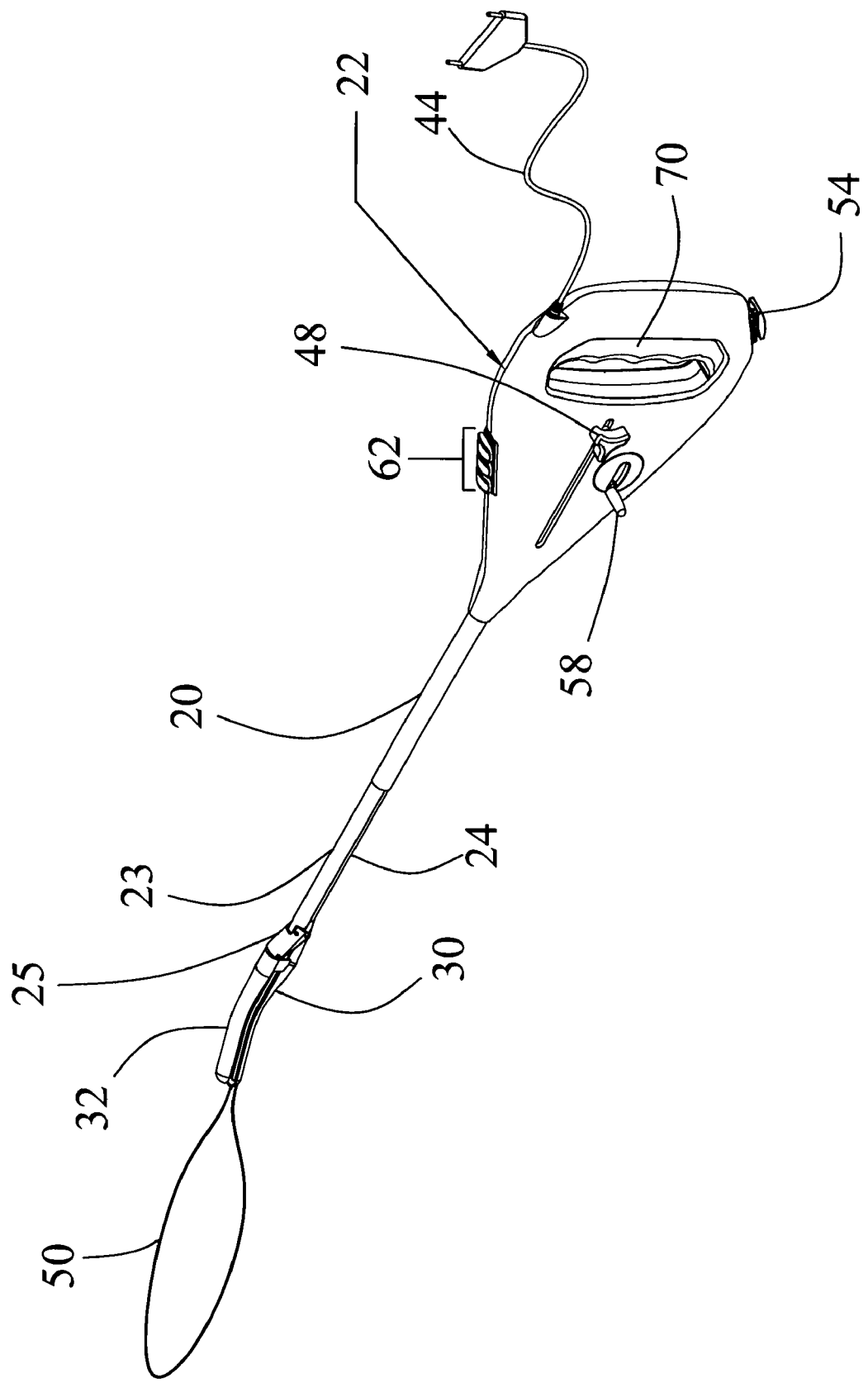
FIG. 1A is another perspective view of the first embodiment of the present invention.

The arrangement of the beams 76, jaw trigger beam engagers 74, jaw trigger 70, translator connector 13, translator 78, and jaw members 30,32 in the embodiment shown in FIGS. 1-2A allow a small amount of travel in the second jaw member 32 to correspond to a larger amount of travel in the jaw trigger 70. That is, the length and orientation of the beams 76, and the manner in which the beams 76 engage the translator 78 cause a specific magnitude of travel (2 millimeters for example) in the jaw member to effect a corresponding but unequal, smaller magnitude of travel in the second jaw member 32 (0.2 millimeters for example). The translation of magnitude of travel from the jaw trigger 70 to the magnitude of travel of the second jaw member 32 also allows the user to transfer more force to the second jaw member 32 at a given force applied to the jaw trigger 70, as is known to those skilled in the art. The specific ratio between jaw trigger 70 travel and the corresponding second jaw member 32 travel may be adjusted for the specific application of the resecting device 10, and therefore, the specific embodiment or ratio achieved thereby in no way limit the scope of the present invention. The arrangement of the jaw trigger 70, beams 76, jaw trigger beam engagers 74, translator connector 13, and translator 78 are one actuating means as recited in the claims.

Figure 3:
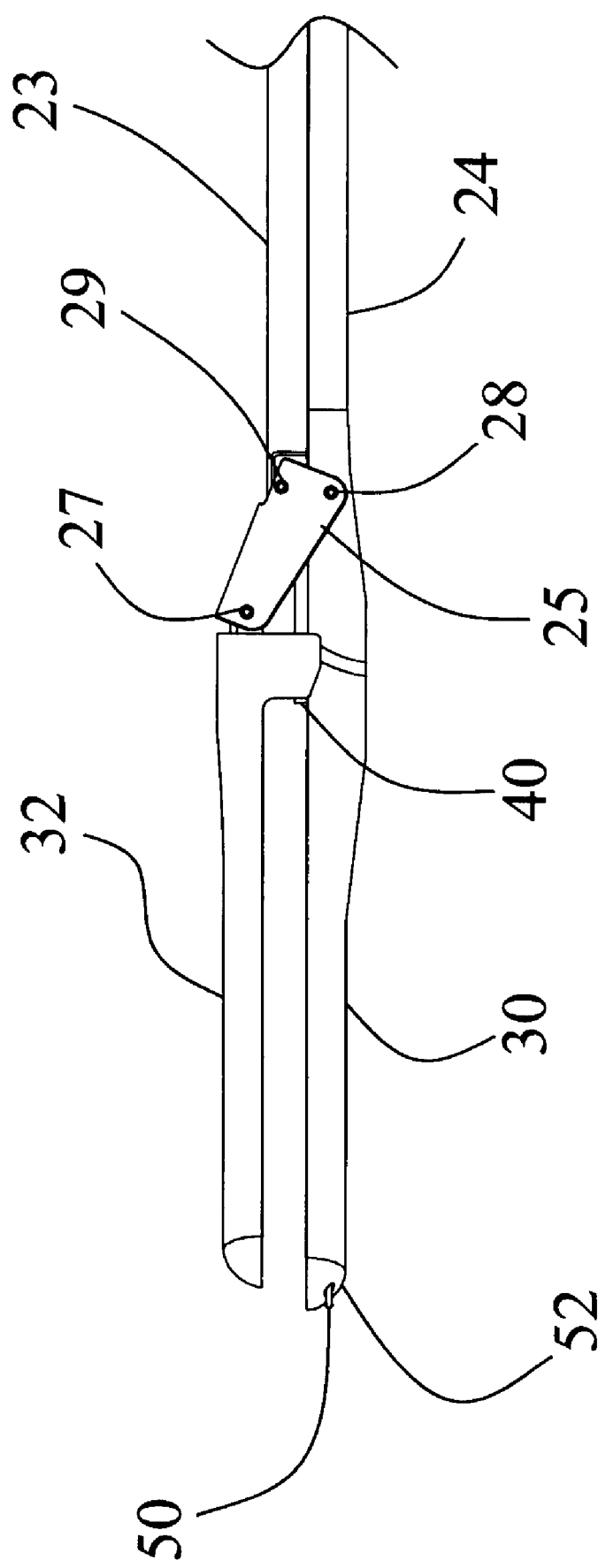
FIG. 3 is a detailed view of the first embodiment of the jaw members.
Figure 3A:
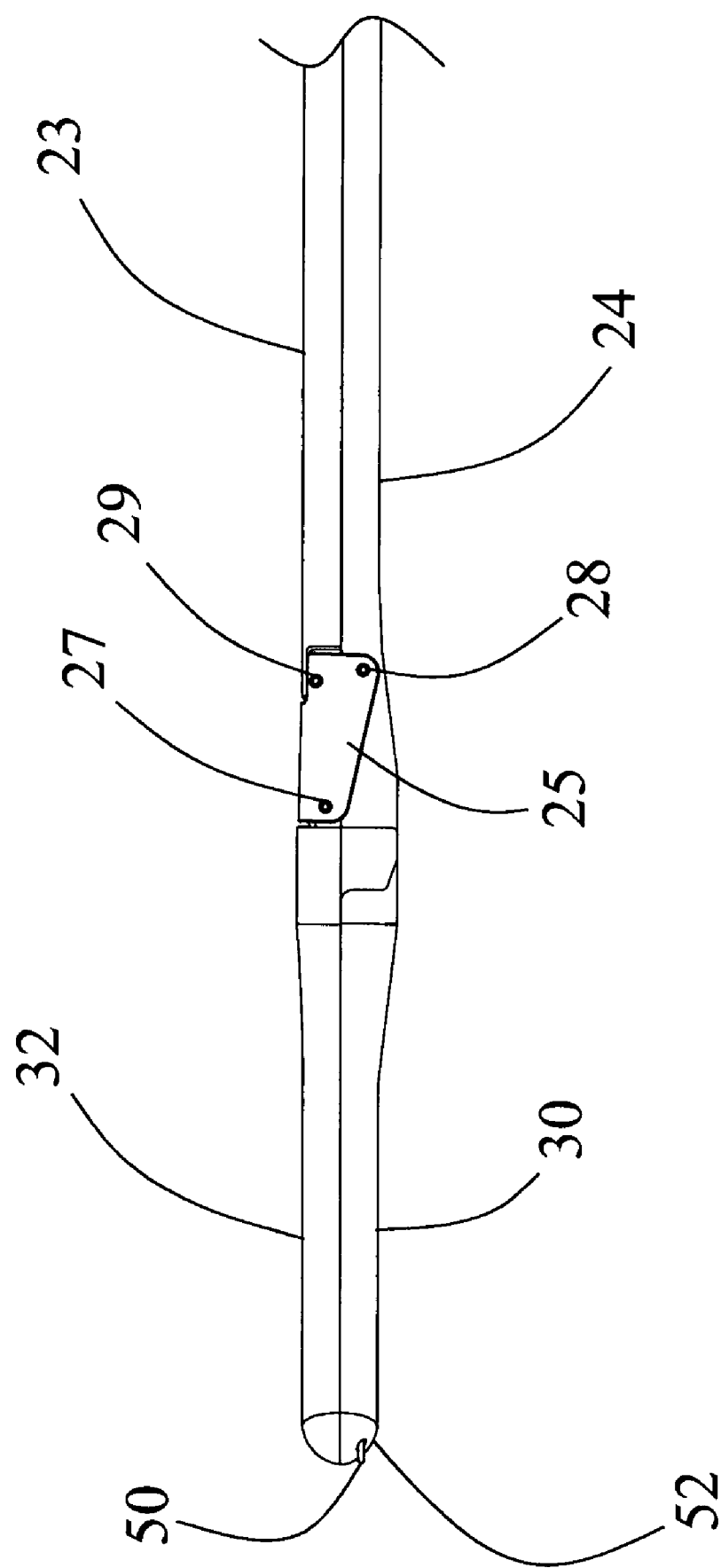
FIG. 3A is another detailed view of the first embodiment of the jaw members.
Figure 3B:
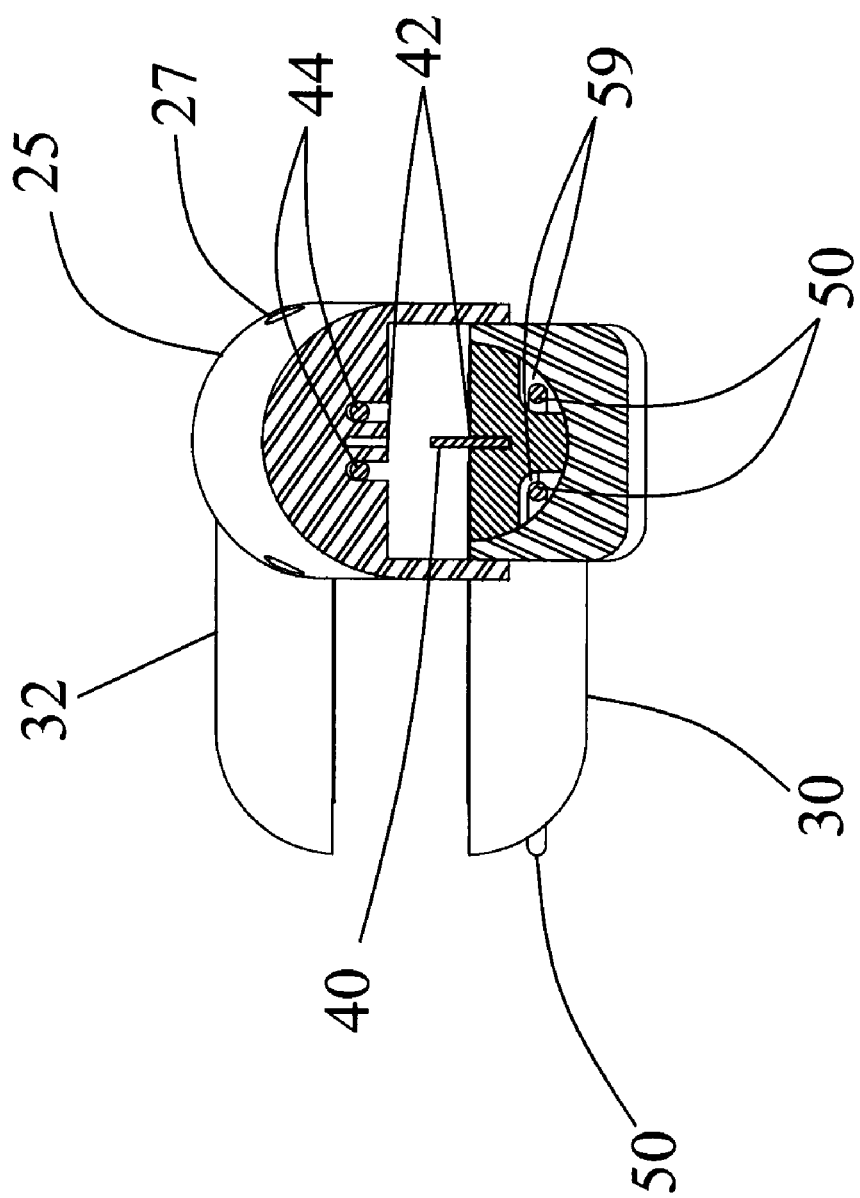
FIG. 3B is a cross-sectional view of the link and the jaw members in the first embodiment of the jaw members.
Figure 7:
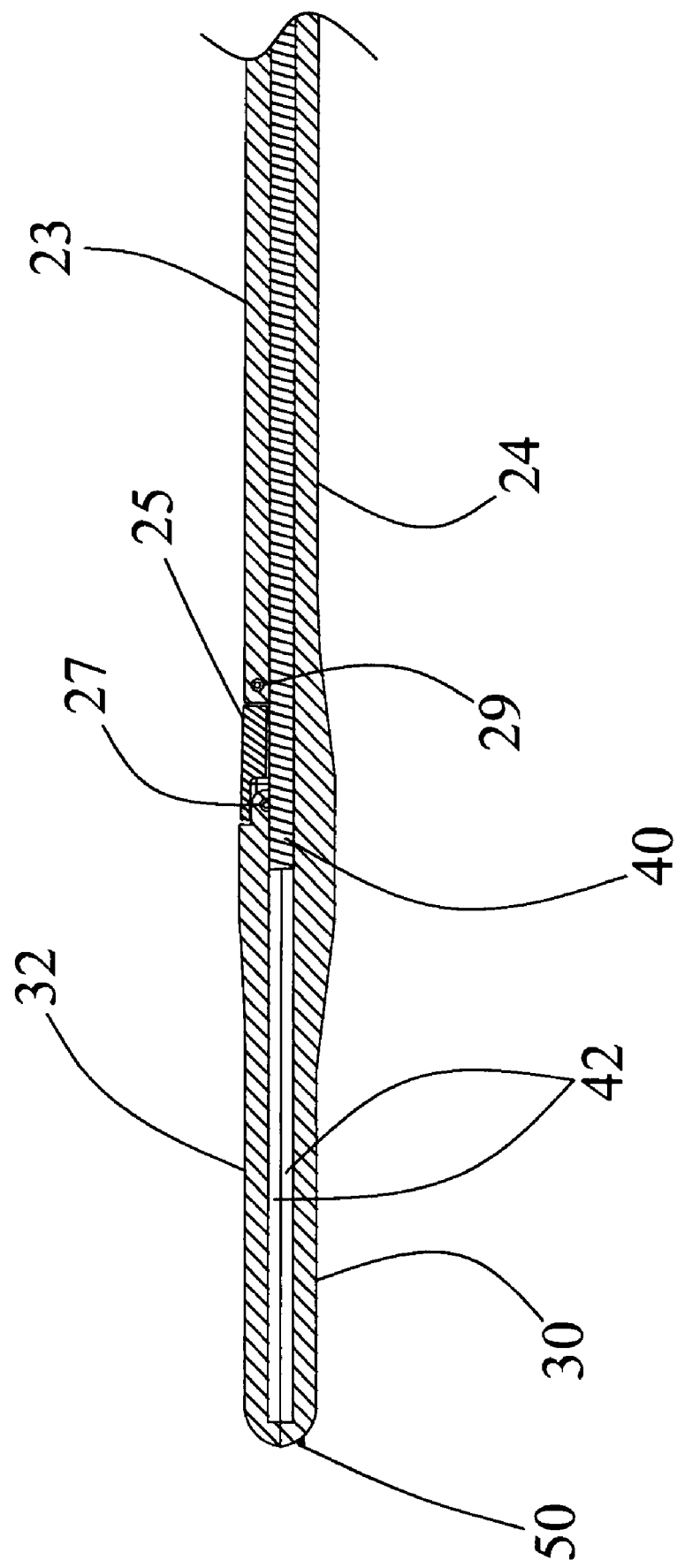
FIG. 7 is a cross-sectional view along the shaft of the first embodiment of the first and second jaw members in a closed position.
Figure 7A:
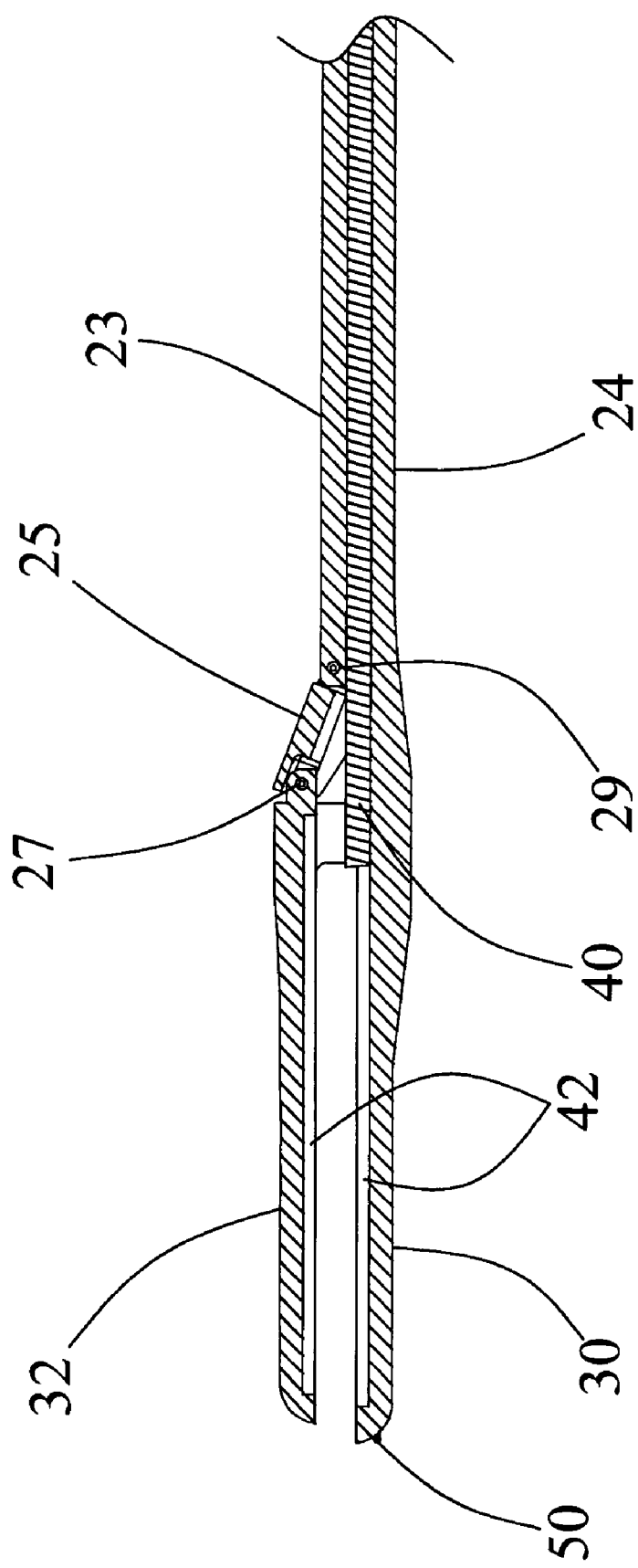
FIG. 7A is a cross-sectional view along the shaft of the first embodiment of the first and second jaw members in an open position.

A detailed view of one embodiment of the first jaw member 30 and second jaw member 32 is shown in FIGS. 3-3B. As shown in FIG. 3, a link 25 serves to communicate forces from the slidable shaft portion 23 to the second jaw member 32 and vice versa. As explained above, the spring mechanism 60 applies a force that causes the first jaw member 30 to be separated from the second jaw member 32 (i.e., the position shown in FIG. 3) unless a user actuates the jaw trigger 70. The second jaw member 32 (with the associated linkage) cooperates with the first jaw member 30 to form a set of cantilevered jaws. As the jaw trigger 70 is actuated, causing the slidable shaft portion 23 to move away from the handle 22 along the axis of the shaft 20, the link 25 moves from the position shown in FIG. 3 to the position shown in FIG. 3A. During this movement, the link 25 pivots about the second jaw member/link connector 27, slidable shaft portion/link connector 29, and fixed shaft portion/link connector 28. The pin 26, pin cap 38 (which functions to secure a pin 26 within pin apertures 36) and associated pin apertures 36 in the link 25 and second jaw member 32 (all of which are best shown in FIG. 10B) make up the second jaw member/link connector 27, which mechanically connects the second jaw member 32 to the link 25. The pin 26, pin cap 38, and associated pin apertures 36 in the link 25 and slidable shaft portion 23 make up the slidable shaft portion/link connector 29, which mechanically connects the slidable shaft portion 23 to the link 25. The pin 26, pin cap 38, and associated pin apertures 36 in the link 25 and fixed shaft portion 24 make up the fixed shaft portion/link connector 28, which mechanically connects the fixed shaft portion 24 to the link 25. Alternative embodiments exist in which structures other than pins 26, pin caps 38, and pin apertures 36 may be used to mechanically connect various moving elements of the resecting device 10 without departing from the scope of the present invention. FIG. 10B best shows the pins 26, pin caps 38, and pin apertures 36 of each of the above-mentioned elements and their relation to one another. To prevent the second jaw member 32 from becoming misaligned with respect to the first jaw member 30, a slot 31 is fashioned in each side of the first jaw member 30 with which two knobs 21 formed on either side of the second jaw member are slidably engaged (best shown in FIG. 10B). FIG. 3B provides a cross-sectional view perpendicular to the axis of the shaft 20 of the link 25, and shows the portion of the link 25 on which the knobs 21 may be located.

A detailed view of an alternative embodiment of the first jaw member 30 and second jaw member 32 is shown in FIGS. 4 and 4A. In this embodiment, a slidable sleeve 12 is slidably engaged with the shaft 20 in an axial direction with respect to the shaft 20. In this embodiment, the shaft 20 is comprised of one portion rather than two portions (as was described for the structure in the previous embodiment having a slidable shaft portion 23 and a fixed shaft portion 24). The second jaw member/link connector 27 is similar to the second jaw member/link connector 27 in the embodiment shown in FIGS. 3-3B, although the associated pins 26, pin caps 38, and pin apertures 36 are not separately shown for the embodiment depicted in FIGS. 4 and 4A. In this embodiment, a portion of the link 25 is within the interior of the shaft 20. The area within the dashed portion of FIG. 4 represents an internal portion of the shaft 20. As the jaw trigger 70 is depressed the slidable sleeve 12 moves towards the jaw members 30, 32, and the distal end (with respect to the handle 22) of the slidable sleeve 12 acts upon the link 25 to urge the second jaw member 32 towards the first jaw member 30. During this motion, the link 25 pivots about the shaft/link connector 14. Two knobs 21 on the second jaw member 32 corresponding to two slots 31 in the first jaw member 30 in this embodiment are similar to the knobs 21 and slots 31 in the embodiment shown in FIGS. 3-3B. The knobs 21 and slots 31 keep the second jaw member 32 from becoming misaligned with the first jaw member 30. A link groove 15 formed in the shaft 20 slidably engages the end of the link 25 opposite the second jaw member/link connector 27 and accounts for difference in the axial length displaced by the link 25 when the second jaw member 32 is actuated from the position shown in FIG. 4 to the position shown in FIG. 4A.

A detailed view of an alternative embodiment of the first jaw member 30 and second jaw member 32 is shown in FIGS. 5 and 5A. This embodiment is similar to the embodiment shown in FIGS. 3-3B, wherein the shaft 20 is formed of a slidable shaft portion 23 and a fixed shaft portion 24. However, the embodiment in FIGS. 5 and 5A uses a second link 16 connected to both the first jaw member 30 and second jaw member 32 in any convenient manner known to those skilled in the art, such as through the use of pins 26 and pin caps 38 in conjunction with pin apertures 36. The second link 16 ensures the second jaw member 32 does not become misaligned with respect to the first jaw member 30. Therefore, two slots 31 fashioned in the first jaw member 30 and two corresponding knobs 21 formed in either side of the second jaw member are not required in this embodiment. The operation of the jaw members 30, 32 is substantially the same in this embodiment as in the embodiment shown in FIGS. 3-3B; however, the useable portion of the jaw members 30, 32 is reduced in this embodiment due to the presence of the second link 16, as can be seen in FIGS. 5 and 5A.

A detailed view of yet another alternative embodiment of the first jaw member 30 and second jaw member 32 is shown in FIGS. 6 and 6A. In this embodiment, both the first jaw member 30 and the second jaw member 32 move during actuation of the jaw trigger 70. In all previous embodiments of the jaw members 30, 32, only the second jaw member 32 moved during actuation of the jaw trigger 70. As in the embodiment shown in FIGS. 4 and 4A, a slidable sleeve 12 is slidably engaged with the shaft 20 in an axial direction with respect to the shaft 20, and the shaft 20 is comprised of one portion rather than two portions. In this embodiment, a separator 18 is positioned between two links 25, one of which is attached to the first jaw member 30 and the shaft 20, and another of which is attached to the second jaw member 32 and the shaft 20. The spring mechanism 60 biases the separator 18 in an axial direction towards the handle 22, and the separator 18 acts upon each respective link 25 to urge the jaw members 30, 32 away from each other. As the jaw trigger 70 is actuated, the slidable sleeve 12 moves along the shaft 20 towards the jaw members 30, 32 and acts upon the respective links 25 to urge the jaw members 30, 32 together. In a manner similar to the embodiment shown in FIGS. 4 and 4A, a pair of link grooves 15 formed in the shaft 20 slidably engage the end of the links 25 opposite the second jaw member/link connector 27 and the corresponding connector on the first jaw member 30. The link grooves 15 account for the difference in the axial length displaced by the link 25 when the jaw members 30, 32 are actuated from the position shown in FIG. 6 to the position shown in FIG. 6A. Two slots 31 in the first jaw member 30 correspond to two knobs 21 formed in the second jaw member 30 to prevent misalignment of the jaw members 30, 32 in the same manner as described for the slots 31 and knobs 21 in the embodiment shown in FIGS. 3-3B.

In all embodiments pictured and described herein, the default position of the jaw members 30, 32 is shown in FIGS. 3, 4, 5, and 6; the position in which the jaw members 30, 32 are separated. However, other embodiments exist in which the default position may be different that those pictured herein. The various embodiments of first and second jaw members 30, 32 pictured in FIGS. 3-6A allow the user to clamp more tissue between the jaw members 30, 32 in one actuation of the jaw trigger 70 than devices of the prior art are able to clamp. This advantage is realized because the distance between the jaw members 30, 32 is constant along the length of the jaw members 30, 32. Because there is no scissoring motion (as there is in devices of the prior art), the extreme distal portion of the jaw members 30, 32 of the present invention are separated by the same distance as the extreme proximal portion of the jaw members 30, 32. This allows the jaw members 30, 32 to be longer when compared to devices in the prior art, so that more tissue may be clamped and electrosurgically treated by the jaw members 30, 32 in one actuation of the jaw trigger 70. Among other advantages this will facilitate a faster surgical procedure, increase accuracy in the tissue to be electrosurgically treated, and result in less blood loss.

Figure 10:
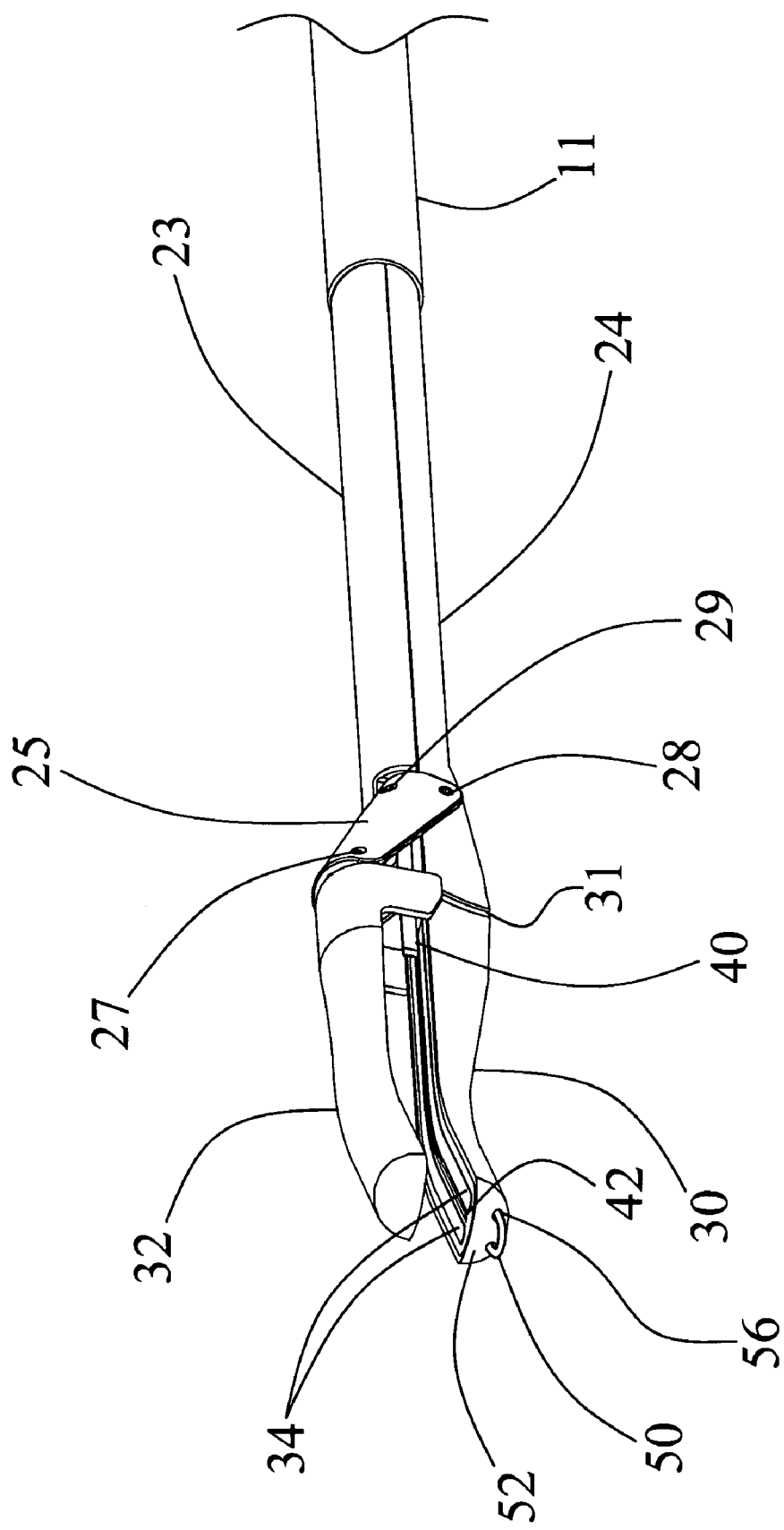
FIG. 10 is a perspective view detailing the jaw members of the first embodiment with the wire loop retracted.
Figure 10A:
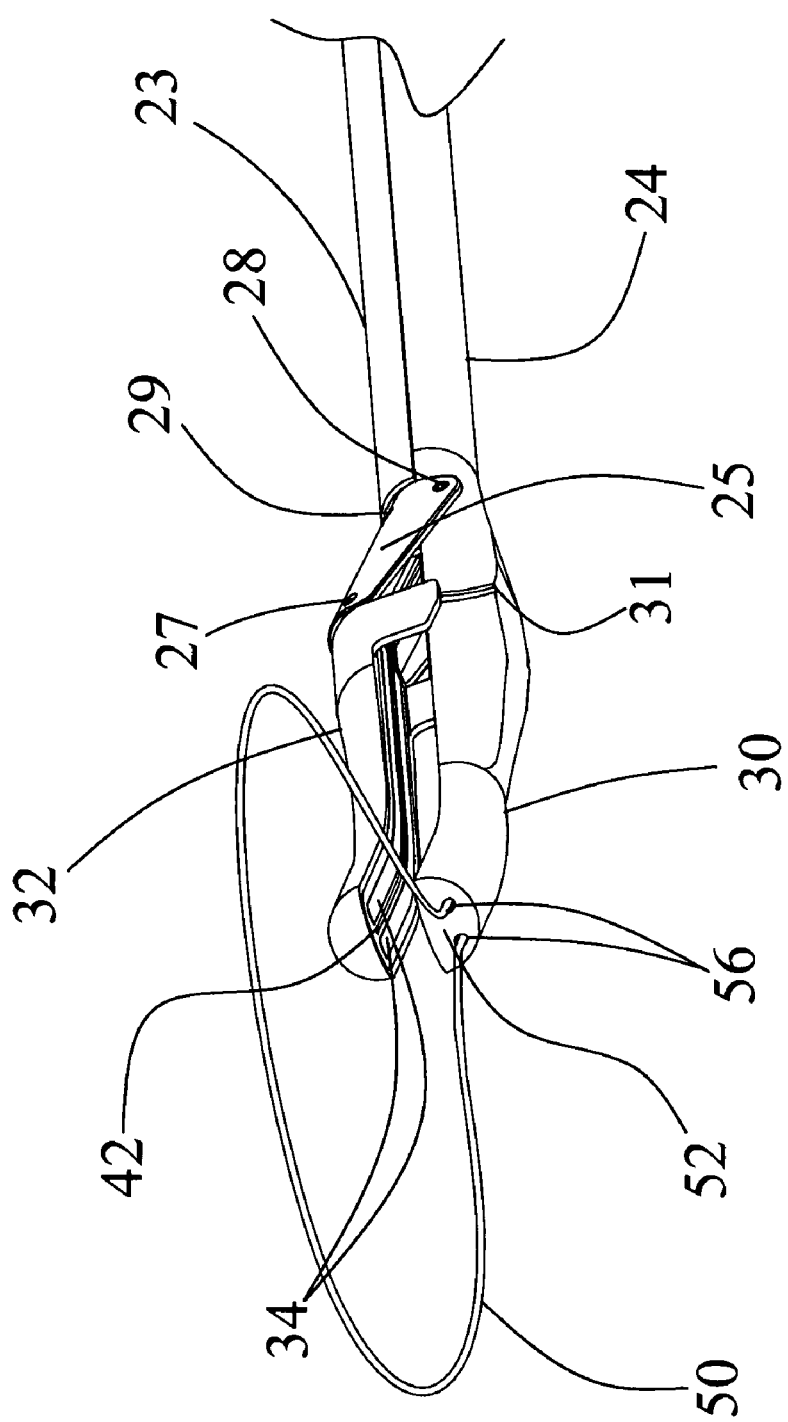
FIG. 10A is another perspective view detailing the jaw members of the first embodiment with the wire loop deployed.
Figure 10B:
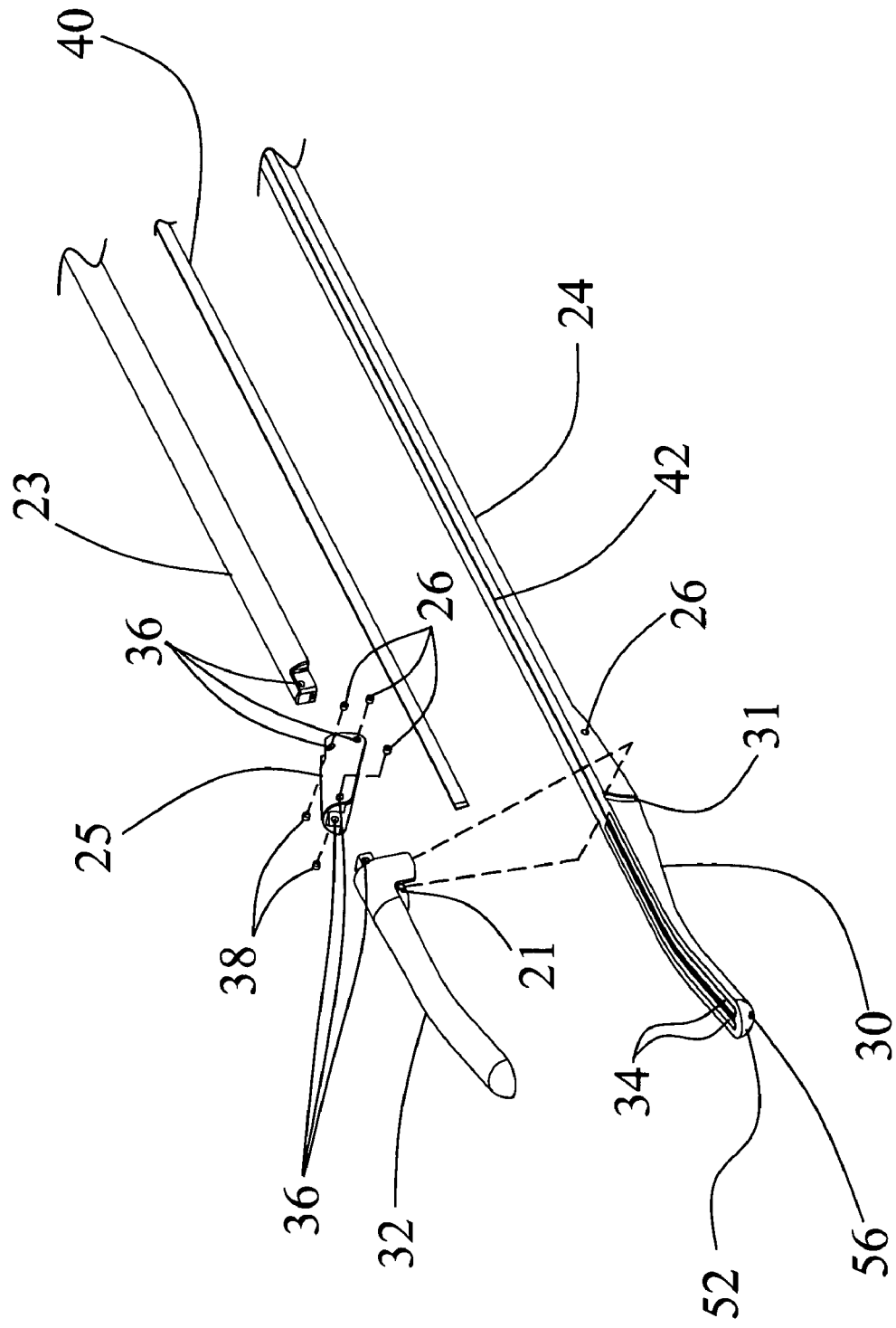
FIG. 10B is an exploded view of the jaw members of the first embodiment.

Both the first jaw member 30 and the second jaw member 32 are fashioned with heavy metal contacts (not shown) that are coated with a nonstick, heat-stable material, such as Teflon or other suitable material known to those skilled in the art, to form the tissue contact areas 34 for each jaw member 30, 32 (best shown in FIGS. 10-10B). A source of electrosurgical energy may be connected to the metal contacts of the jaw members 30, 32 (the electrosurgical energy may be routed through an electrode selector 62, as explained in detail below) via electrical conduit 44. Electrical conduit 44 is one means of connecting the tissue contact areas 34 to a source of electrosurgical energy as recited in the claims. The tissue contact areas 34 may serve as dual-sequencing, electrosurgical energy tissue gripping electrodes for conducting electrosurgical energy to tissues in contact with the tissue contact areas 34 of the jaw members 30, 32. That is, the tissue contact area 34 on the first jaw member 30 may serve as one electrode, and the tissue contact area 34 on the second jaw member 32 may serve as a second electrode for conducting electrosurgical energy through tissue between the jaw members 30, 32. The tissue contact areas 34 may extend along the entire gripping surface of the jaw members 30, 32 or only a portion thereof, depending upon the specific embodiment. The non-stick coating on the tissue contact areas 34 prevents coagulated blood or electrosurgically treated tissue from sticking to the tissue contact areas 34. Sticky tissue coagulum may rip fragile electrosurgically treated tissue while attempting to pull the jaw members 30, 32 off of the electrosurgically treated tissue, resulting in bleeding. In one embodiment, a semiconductor chip (not shown) alternates electrosurgical energy (which may be in any frequency and amplitude that the source of electrosurgical energy is capable of delivering, including Rf frequencies) between the heavy metal contacts on the jaw members 30, 32. The semiconductor chip, which may be positioned within the handle 22 or in any similarly convenient location, alternates the electrosurgical energy off and on to allow maximal electrosurgical treatment of tissue with minimal lateral thermal spread; thereby ensuring a minimal amount of tissue outside the tissue contact areas 34 is affected by the electrosurgical energy. Based on tissue resistance feedback, the semiconductor chip will alternate the current. Higher power settings will cause faster current oscillation than lower power settings will cause. This alternating of electrosurgical energy will produce more even deposition of thermal energy across the tissue contact areas 34. The tissue contact areas 34 may take other shapes and orientations without departing from the spirit and scope of the present invention, and the semiconductor chip may be located in any portion of the resecting device 10 that is convenient, or it may be located external from the resecting device 10, as dictated by the specific application.

In the exemplary embodiment of the jaw members 30, 32, the jaw members 30, 32 are curved to match the curvature of the outer wall of a human uterus, as is best shown in FIGS. 8A-8D; although other curvatures of the jaw members 30, 32 are included within the scope of the present invention, including straight jaw members 30, 32. In an alternative embodiment not pictured herein, the shaft 20 could be curved to facilitate a specific surgical procedure other than a hysterectomy. Throughout FIGS. 8A-8D the dashed line represents the blade track 42 passing through the shaft 20 and the jaw members 30, 32. As shown in FIGS. 8A-8D, the curvature of the jaw members 30, 32 may be derived from circles having different radii, depending on the specific embodiment. Although not shown, the jaw members 30, 32 may also have different angles between the straight shaft 20 portion proximate the handle 22 and the straight jaw member 30, 32 portion distal the curvature in the shaft 20 and/or jaw members 30, 32. In the embodiments shown in FIGS. 8A-8D, this angle (i.e., the angle between the straight jaw member 30, 32 portion distal the curvature in the jaw members 30, 32 and the straight shaft 20 portion proximate the handle 22) is denoted "A," and has a value of twenty degrees. In the several embodiments shown in FIGS. 8A-8D, the linear difference between the straight shaft 20 portion and the distal end of the jaw members 30, 32 is 15 millimeters. That is, the end of the jaw members 30, 32 is offset from the straight portion of the shaft 20 by 15 millimeters. However, depending on the particular embodiment or the particular use to which the resecting device 10 is put, this distance may be adjusted as needed without departing from the spirit and scope of the present invention.

Figures 8A, 8B, 8C, 8D:
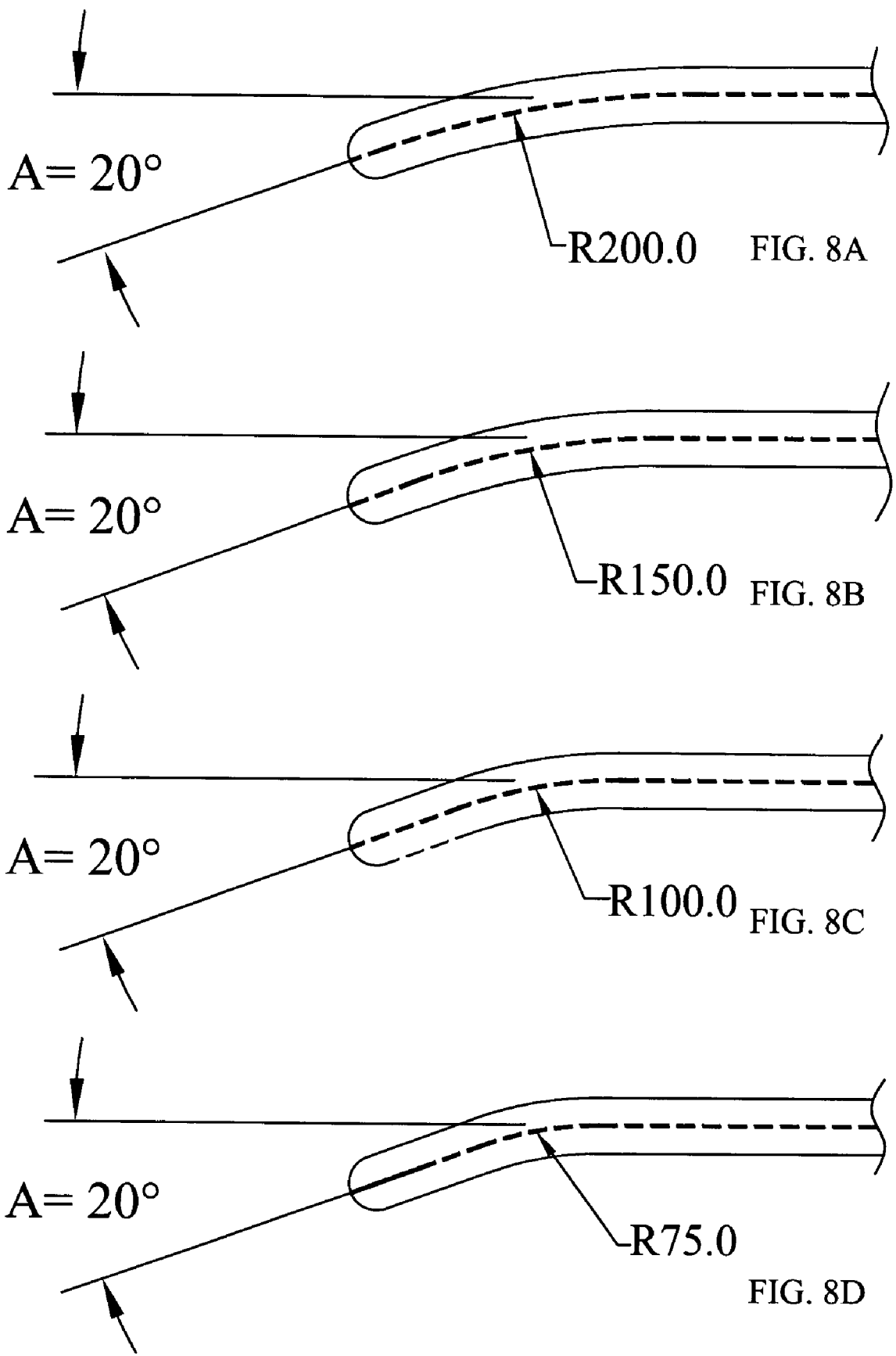
FIG. 8A is a dimensional view of a first embodiment of the curvature of the jaw members.
FIG. 8B is a dimensional view of a second embodiment of the curvature of the jaw members.
FIG. 8C is a dimensional view of a third embodiment of the curvature of the jaw members.
FIG. 8D is a dimensional view of a fourth embodiment of the curvature of the jaw members.
Figure 9:
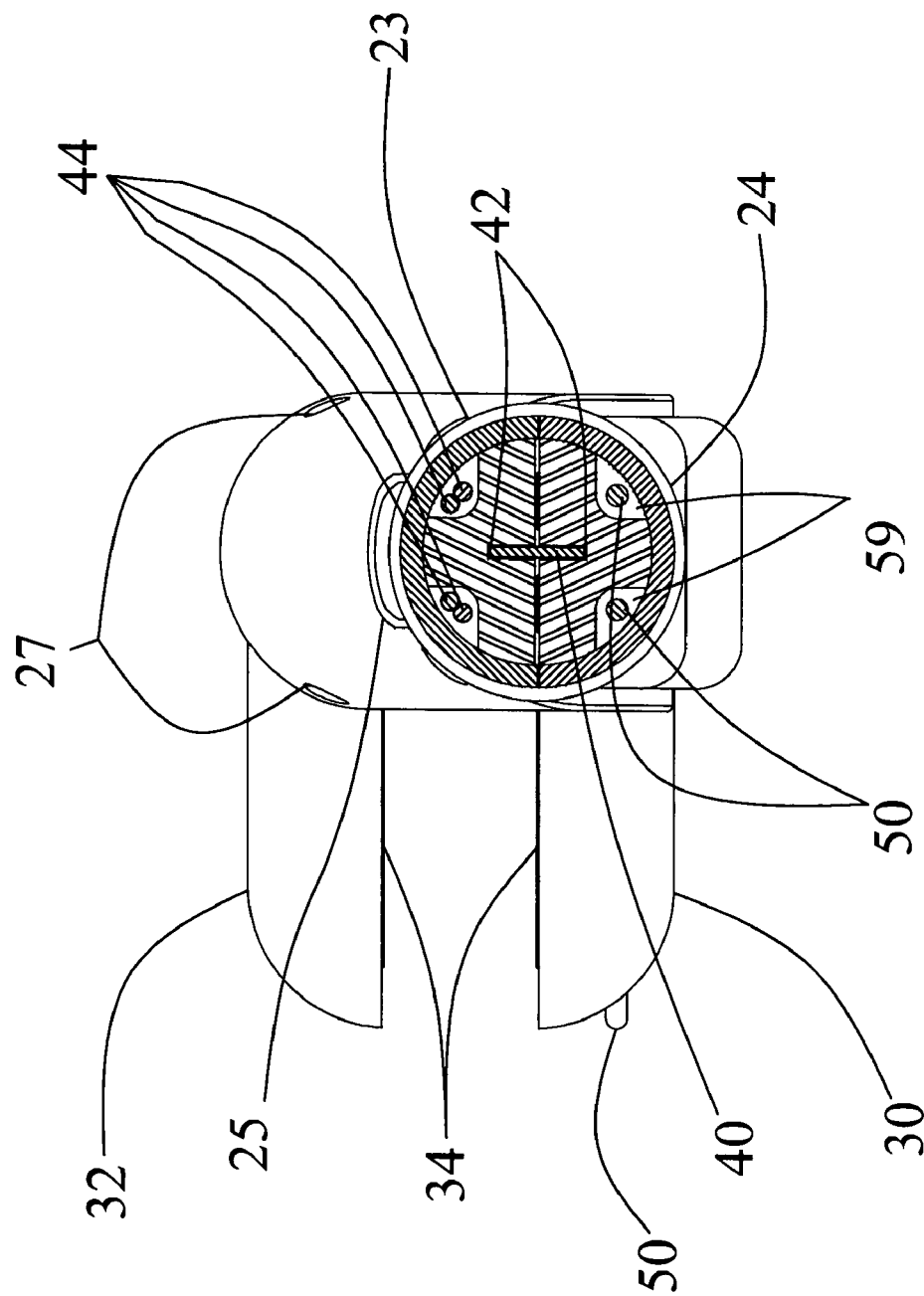
FIG. 9 is a cross-sectional view of the shaft of the first embodiment.

The embodiment shown in FIG. 8A represents a curvature resulting from a circle having a radius of 200 millimeters. The embodiment shown in FIG. 8B represents a curvature resulting from a circle having a radius of 150 millimeters, and the embodiments in FIGS. 8C and 8D show the curvature resulting in circles having radii of 100 millimeters and 75 millimeters, respectively. As is clear from FIGS. 8A-8D, the smaller the radius of the circle used to create the curvature, the sharper and more abrupt the curvature appears. Variations and alterations to the curvatures and there respective lengths in the embodiments disclosed herein will occur to those skilled in the art without departing from the scope of the present invention.

The blade 40 operates along the blade track 42, which runs through both the slidable shaft portion 23 and fixed shaft portion 24 of the shaft 20, the link 25 (depending on the particular embodiment), and the jaw members 30, 32. The orientation of the blade track 42 for the exemplary embodiment is best shown in FIGS. 3B, 7A, 7B, 9, and 10B. The blade 40 is used to divide tissue held between the jaw members 30, 32. In the embodiments pictured herein, the blade 40 and blade track 42 are fashioned to be such a dimension so that when the jaw members 30, 32 abut one another (as shown in FIGS. 3A, 4A, 5A, and 6A) enough clearance remains so that the blade 40 may pass through the portion of the blade track 42 that extends through the jaw members 30, 32. In the embodiments pictured herein, the blade 40 extends the entire length of the shaft 20 and is directly connected to the blade actuator 46. In an alternative embodiment, the blade 40 may be mechanically engaged with an insulated blade assembly (not shown), which subsequently may be connected to the blade actuator 46. The blade 40 (or blade assembly, depending on the particular embodiment) may also be connected to a source of electrosurgical energy, either through direct contact by an electrical conduit 44, such as wire or a conductive hub, or by a series of monopolar conductive elements (either directly or through the electrode selector 62, as explained below). The arrangement of the blade 40, blade track 42, blade actuator 46, and blade assembly (if present) comprise one type of mechanical resecting means as recited in the claims.

If the particular embodiment includes a blade assembly, the blade assembly must be electrically insulated so that when the blade 40 is energized, electrosurgical energy does not flow from the blade 40 to the blade assembly, or from the blade assembly to other conductive components in the resecting device 10. If a blade assembly is not used (i.e., the blade 40 is connected directly to the blade actuator 46), the portion of the blade 40 that is enclosed in the shaft 20 must be electrically insulated, either by applying an insulating material to the outside surface of the blade 40 or by ensuring all portions of the resecting device 10 that come in contact with the blade 40 (primarily the blade track 42) are electrically insulating. When energized, the blade 40 serves as one electrode and the tissue contact area 34 of the first jaw member 30, the second jaw member 32, or both serve as the corresponding electrode to create a bipolar means to deliver electrosurgical energy to tissue in contact with the blade 40. The position of the blade 40 along the blade track 42 is determined by the position of the blade actuator 46, which is slidably engaged with the handle 22. That is, the blade actuator 46 moves relative to the handle 22, and the blade 40 (and blade assembly, depending on the embodiment) moves in the same direction and with the same magnitude. The limits of blade 40 travel along the blade track 42 will vary depending on the specific embodiment, but typically the blade will travel at least the axial length of the tissue contact areas 34. In other embodiments not shown herein, the blade track 42 extends to the most distal portion of the jaw members 30, 32 and the blade actuator 46 and handle 22 are configured so that the blade 40 may be extended a small distance beyond the distal end of the blade track 42 to ensure any tissue between the jaw members 30, 32 is divided upon full actuation of the blade 40.

The wire loop 50 is situated at the distal end (with respect to the handle 22) of the shaft 20, and in the exemplary embodiment protrudes from the first jaw member 30 through two wire apertures 56, which is best shown in FIGS. 10 and 10A. The wire loop 50, a portion of which is positioned in the interior of the handle 22 in the exemplary embodiment but may be positioned elsewhere in alternative embodiments, extends through an electrically insulated conduit 59 (which is located within the shaft 20 and relevant portions of the handle) to the wire spool 53. The wire loop 50 may be made of any suitable material that is capable of conducting electrosurgical energy and provides sufficient flexibility, such as a polymer coated ferrous metal, or any other suitable material known to those in the art that is suitable for the conditions in which the resecting device 10 will be used. The wire spool 53 is also positioned in the interior of the handle 22 in the exemplary embodiment. The wire spool 53 is mechanically engaged with an electric motor 51, which causes the wire spool 53 to rotate in one of two directions depending on the position of the wire loop switch 54. In the embodiment shown in FIGS. 1 and 2, the wire loop switch 54 is located exterior to the handle 22 and is easily accessible by the thumb of the user. The wire loop switch 54 is in electrical communication with the electric motor 51, and the position of the wire loop switch 54 controls the operation of the electric motor 51. In a first position of the wire loop switch 54, the electric motor 51 rotates the wire spool 53 a direction that causes the wire loop 50 to deploy distally from the shaft 20, as shown in FIG. 10A. In a second position of the wire loop switch 54, the electric motor 51 rotates the wire spool 53 in a direction opposite to the direction it rotates when the wire loop switch 54 is in the first position, and the wire loop 50 retracts towards the distal end of the shaft 20, as shown in FIG. 10. The wire loop switch 54 includes a third position in which the electric motor 51 is not energized and therefore does not rotate in either direction. A wire loop handle 58 may also be mechanically engaged with the wire spool 53 to manually retract and deploy the wire loop 50. The electric motor 51 may be powered by a battery (not shown), or it may be powered from a typical wall outlet through the use of appropriate circuitry, as is well known to those skilled in the art (shown in FIG. 11).

When fully retracted, the wire loop 50 rests against the contact plate 52, which is affixed to the distal end of the first jaw member 30 in the exemplary embodiment, and is best shown in FIGS. 10 and 10A. As noted above, the wire loop 50 protrudes from the first jaw member 30 through wire apertures 56. As is well known to those skilled in the art, the contact plate 52 may be placed at other distal positions along the shaft 20 without departing from the spirit and scope of the present invention. When fully deployed, the wire spool 53 is essentially empty of all wire and the wire loop 50 has its largest periphery, which may vary depending on the specific embodiment; when fully retracted, a larger portion of the wire is engaged with the wire spool 53 and the wire loop 50 has its smallest periphery. The wire loop 50 may also be connected to a source of electrosurgical energy, either through direct contact by an electrical conduit 44, such as wire or a conductive hub, or through a series of mono-polar conductive elements (either directly or through the electrode selector 62, as explained below). When the wire loop 50 is energized, the contact plate 52 acts as the ground for the wire loop 50 to form a bipolar electrosurgical circuit. The arrangement of the wire loop 50 and wire spool 53 comprise one loop means as recited in the claims.

Figure 11:
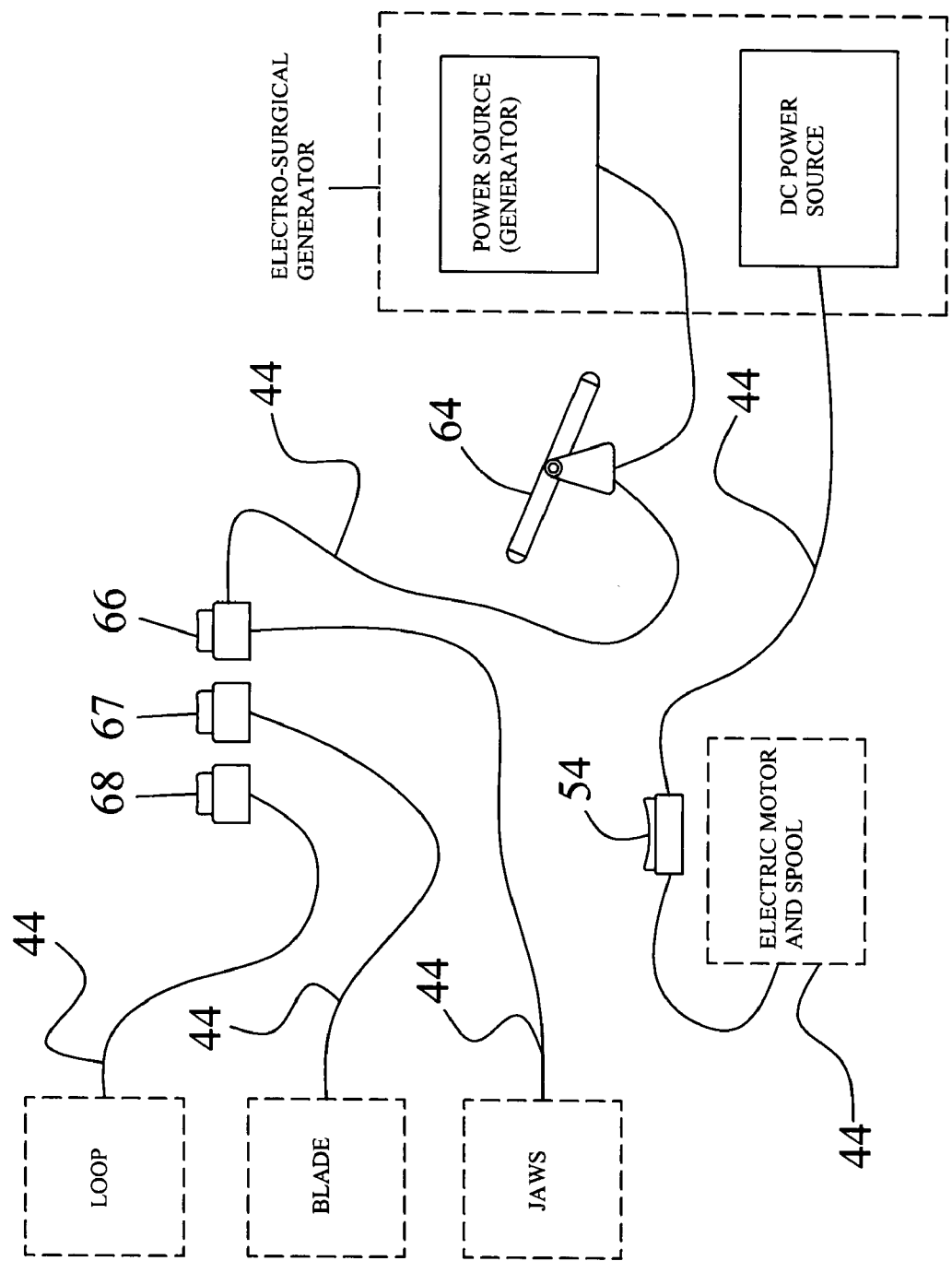
FIG. 11 is a schematic diagram of the electrosurgical energy paths in one embodiment of the resecting device.

In any embodiment of the resecting device 10 in which more than one element may be energized with electrosurgical energy, an electrode selector 62 is employed to select the elements to be energized. FIG. 11 provides a simplified schematic diagram of the circuitry of one embodiment of the resecting device 10. In the exemplary embodiment, the electrode selector 62 is placed so that a portion of the electrode selector 62 is exterior to the handle 22 in a position easily accessible to the user. This portion of the electrode selector consists of the jaw button 66, blade button 67, and loop button 68. As noted, FIG. 11 provides a simplified schematic diagram of how several electrodes (tissue contact areas 34, blade 40, wire loop 50) may be in communication with a source for electrosurgical energy through the electrode selector 62. In one embodiment, the source for electrosurgical energy is in direct communication with a foot pedal 64 that must be depressed to allow the electrosurgical energy to travel from the source of electrosurgical energy to the electrode selector 62. With the foot pedal 64 depressed, a specific position of the electrode selector 62 will cause the electrode corresponding to that position to be energized with electrosurgical energy. If the jaw button 66 is pressed, the electrode selector 62 will allow the tissue contact areas 34 of the jaw members 30, 32 to be energized with electrosurgical energy; if the blade button 67 is pressed, the electrode selector will allow the blade 40 to be energized with electrosurgical energy; and if the loop button 68 is pressed, the electrode selector 62 will allow the wire loop 50 to be energized with electrosurgical energy. The electrode selector 62 is preferably a lockout style switch that allows only one element to be energized at any given time. That is, if the jaw button 66 is pressed, the electrode selector will not allow electrosurgical energy to pass to the blade 40 or the wire loop 50. The user interface of the electrode selector 62 (the respective buttons 66, 67, and 68) may be illuminated to facilitate selection of the proper electrode in low-light environments. Illumination of the buttons 66, 67, 68 may be accomplished by placing an illuminating bulb (not shown) inside the handle 22, by making the buttons 66, 67, 68 from a material that glows after exposure to light, or by any other means known in the art. The buttons 66, 67, 68 may also be fashioned so that they are resistant to water by hermetically sealing the interface between the buttons 66, 67, 68 and the electrode selector 62, as is known in the art. This sealing may be accomplished through appropriate glue, thermoforming of plastic, or any other suitable means known to those skilled in the art. In the exemplary embodiment, the buttons 66, 67, 68 are fashioned of a translucent flexible material, such as silicon, polyethylene, polypropylene, or other suitable material. In the exemplary embodiment, the jaw button 66 is green, the blade button 67 is yellow, and the loop button 68 is red, so that the user can easily distinguish among the buttons 66, 67, 68.

In embodiments of the resecting device 10 in which only two elements are connected to a source of electrosurgical energy, the electrode selector 62 would only require two positions to operate properly. In other embodiments not pictured herein, the electrode selector 62 may have multiple positions, including a first position for energizing the blade 40, a second for energizing the first jaw member 30, a third for energizing the second jaw member 32, and a fourth for energizing the wire loop 50. The electrode selector 62 may have other positions as well, such as different positions to specify which jaw member 30, 32 serves as the ground electrode when the blade 40 is energized. Accordingly, the specific positions, how the positions are arranged, and combinations of positions and arrangements thereof in any embodiment of the electrode selector 62 in no way limit the spirit or scope of the present invention. The arrangement of the electrical conduit 44, wire loop 50, contact plate 52, wire spool 53, wire loop switch 54, insulated conduit 59, electrode selector 62, foot pedal 64, jaw button 66, blade button 67 and loop button 68 comprise one means to connect and/or actuate the source of electrosurgical energy with the gripping means and/or loop means as recited in the claims. Additionally, the arrangement of the electrode selector 62, foot pedal 64, jaw button 66, blade button 67 and loop button 68 comprise an energy selector means as recited in the claims.

The following describes a procedure for using one embodiment of the resecting device 10 in laparoscopic or endoscopic surgery. As previously noted, the resecting device 10 may be used in any type of surgical procedure in which the user would find the resecting device 10 convenient, and any specific method of use or surgical procedure described herein in no way limits the scope of the present invention.

Figures 12A, 12B, 12C, 12D:
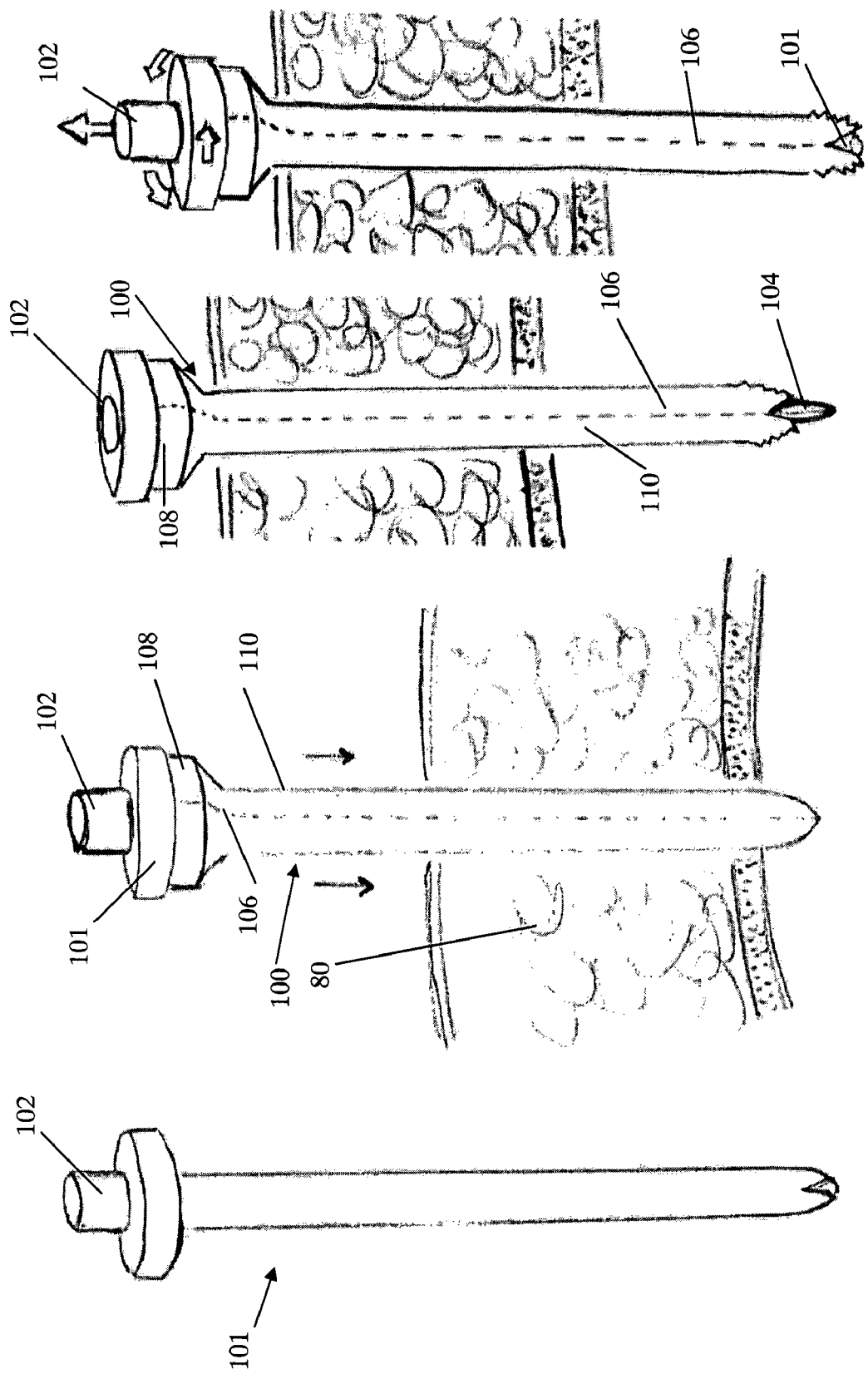
FIG. 12A is a detailed view of one embodiment of the trocar not engaged with the introducer sheath.
FIG. 12B is a detailed view of the trocar engaged with the introducer sheath being inserted into the abdominal wall.
FIG. 12C is a detailed view of one embodiment of the trocar engaged with the introducer sheath after the trocar button has been pushed to pierce the introducer sheath.
FIG. 12D is a detailed view of the introducer sheath engaged with the trocar showing how the trocar is removed from the introducer sheath.
Figure 12G:
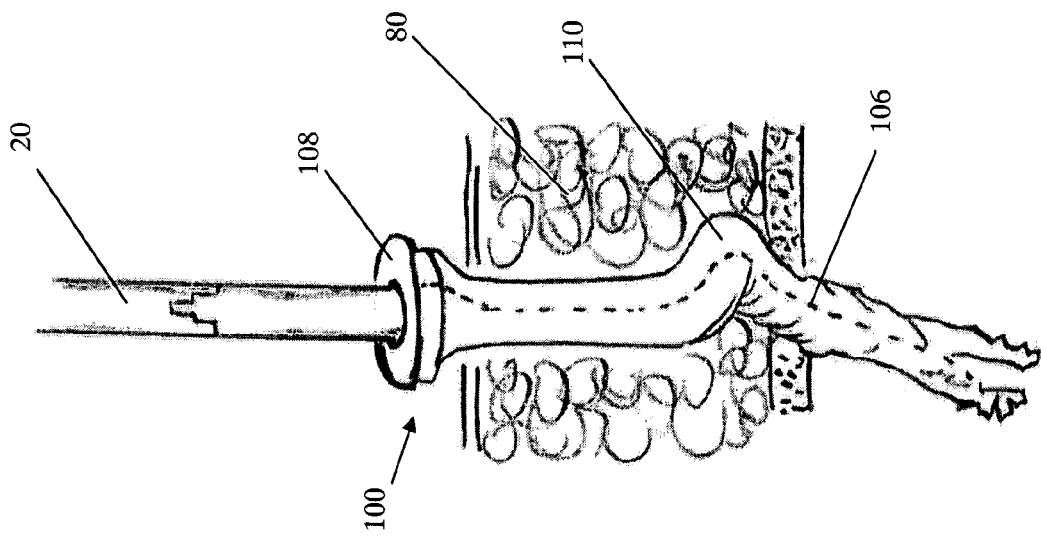
FIG. 12G is a detailed view of the resecting device being inserted through the abdominal wall through the introducer sheath.
Figure 12F:
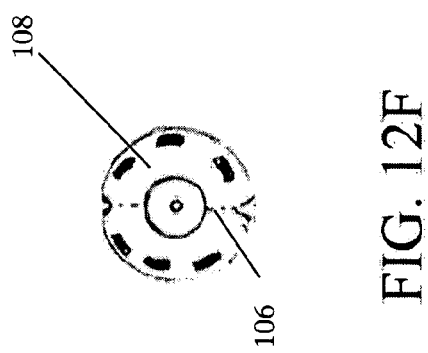
FIG. 12F is a detailed view of the top of the introducer sheath showing the introducer sheath ring.
Figure 12E:
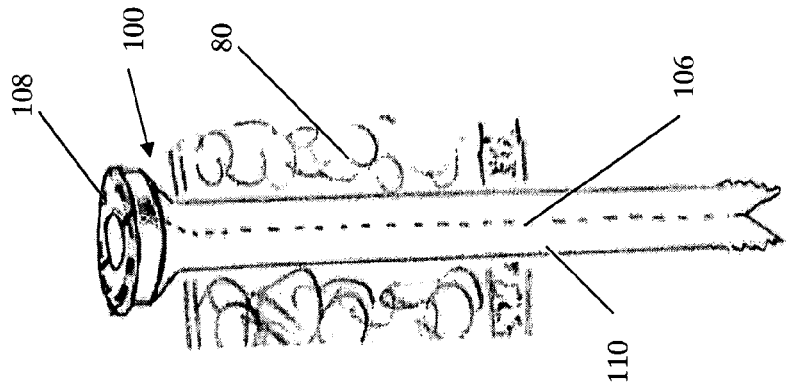
FIG. 12E is a detailed view of the introducer sheath passing through the abdominal wall after the trocar has been removed.

After a penetrating trocar (not shown) has been used to provide a path through the abdominal wall 80 into the interior of the subject of the operation, a specialized trocar 101 shown in FIG. 12A, constructed of any material known by those skilled in the art to be appropriate for a specific application (such as metal, polymer, composite, etc.), is outfitted with a perforated flexible introducer sheath 100 (shown in FIGS. 12B-13) around the outer surface of the trocar 101. The introducer sheath 100 may be constructed of any flexible material suitable for the specific surgical procedure. In one embodiment, the introducer sheath 100 will be constructed of latex rubber having a thickness from 0.001 millimeter to 1 millimeter. The introducer sheath 100 is fashioned with perforations 106 along the length of the introducer sheath body 110 so that it may be separated and removed from a surgical instrument at any time during the procedure. The perforations 106 may extend along one or more axial planes for the length of the introducer sheath 100. The introducer sheath 100 is also fashioned with an introducer sheath ring 108 on the portion of the introducer sheath 100 that is exterior to the patient. The introducer sheath ring 108 provides the site for entry of a surgical instrument into the introducer sheath 100 and ensures the introducer sheath 100 does not slip into the incision. The introducer sheath ring 108 also ensures that a portion of the introducer sheath 100 will remain accessible and visible if the user desires to remove the introducer sheath 100. The introducer sheath ring 108 may be made of the same material as the introducer sheath body 110, or of another suitable material for the specific application, which material imparts sufficient rigidity to the introducer sheath ring to allow the user to easily grasp and remove the introducer sheath 100.

Figure 13:
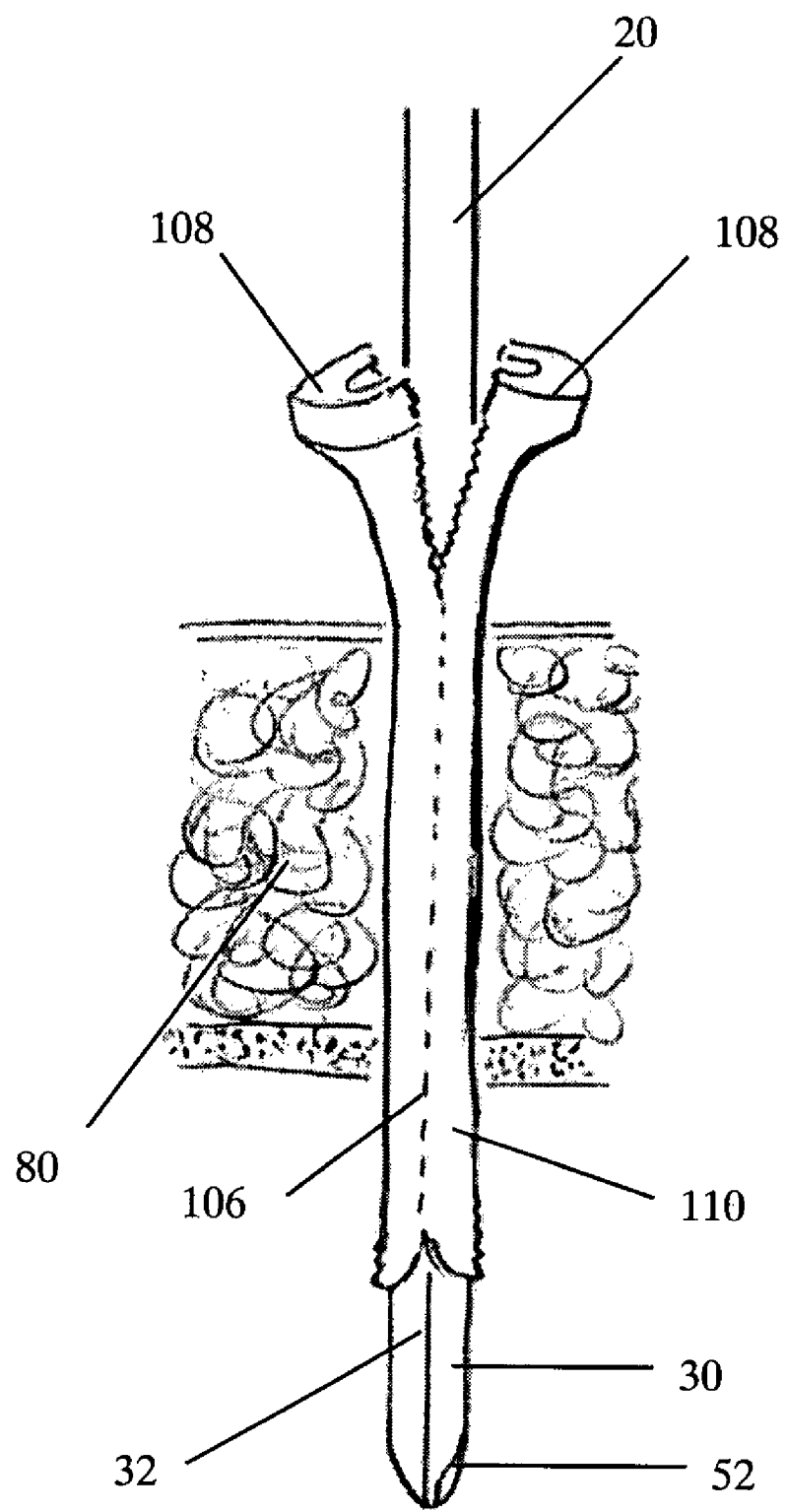
FIG. 13 is a detailed view of the introducer sheath engaged with the resecting device showing the introducer sheath being separated along the perforations.

The end of the introducer sheath 100 opposite the introducer sheath ring 108 is closed (as shown in FIG. 12B), but may be easily pierced with the proper tool, as described in detail below. To remove the introducer sheath 100, the user may simply grasp a portion of the introducer sheath ring 108 on either side of the perforations 106 and pull the respective portions up and away from the incision, causing the introducer sheath 100, including the introducer sheath body 110 and introducer sheath ring 108, to divide along the perforations 106, as shown in FIG. 13. In an alternative embodiment not pictured herein, the perforations 106 do not extend along the entire length of the introducer sheath 106.

Figure 14:
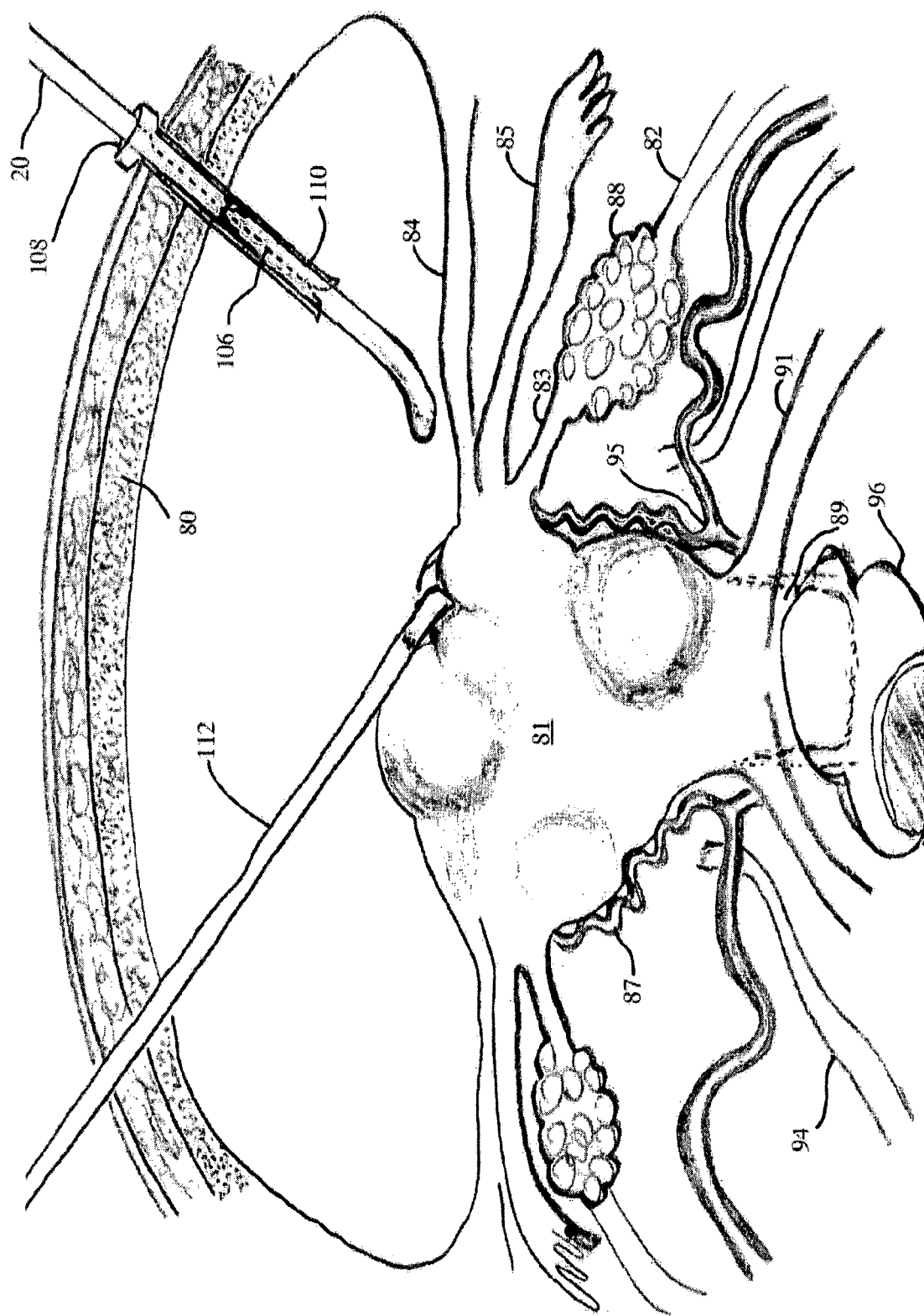
FIG. 14 is a detailed view of one embodiment of the resecting device positioned within a human abdomen.

To position the introducer sheath 100, the trocar 101 and the introducer sheath 100 are inserted into the abdominal cavity through the incision and path through the abdominal wall 80 created by the penetrating trocar. When the inserted end of the trocar 101 has passed through the abdominal wall 80, the user presses the trocar button 102, which causes a stylus 104 within the trocar 101 to protrude through the inserted end of the trocar 101 and pierce the corresponding end of the introducer sheath 100, as shown in FIG. 12C. The trocar 101 is then removed from the introducer sheath 100 and the resecting device 10 is inserted through the introducer sheath 100 into the same incision and path (as shown in FIG. 12G) in the abdominal wall 80. The surgical instrument is then positioned according to the surgical procedure to be undertaken, as shown in FIGS. 14 and 15, which corresponds to procedures involving a hysterectomy. The flexible design of the introducer sheath 100 accommodates the curved jaw embodiments of the resecting device 10. The presence of the introducer sheath 100 in the incision mitigates the possibility of the user placing the resecting device 10 in an improper location (e.g., straying into subcutaneous, preperitoneal, or rectus muscle compartments). The introducer sheath 100 also facilitates timely placement of the resecting device 10 in the area of the patient where the surgery is to take place. The introducer sheath 100 is designed to be removable so that if it slips down the shaft 20 of the resecting device 10 towards the patient, the user may remove the introducer sheath 100 prior to its interference with the actuation of the jaw members 30, 32.

Figure 17:
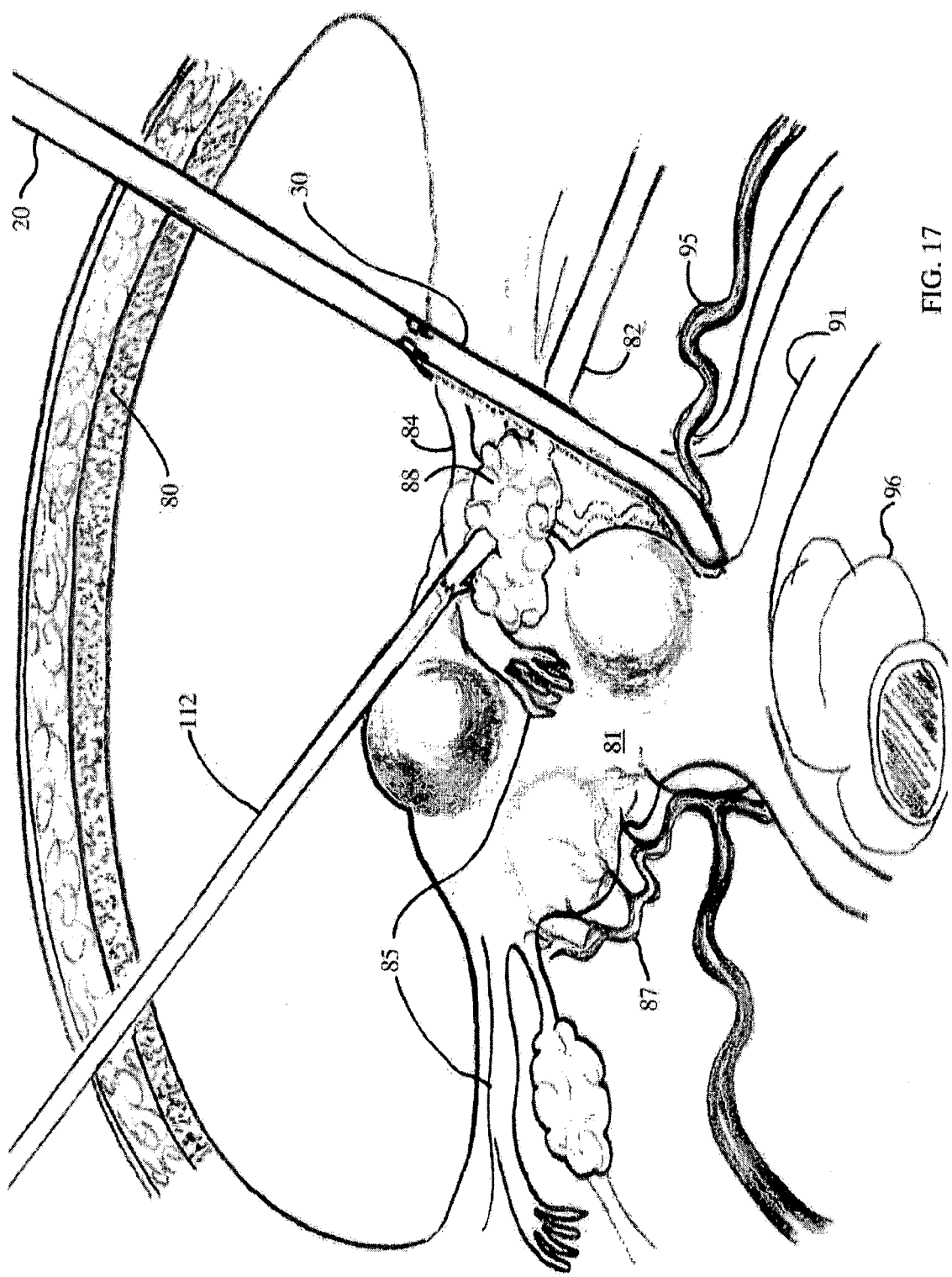
FIG. 17 is a detailed view of one embodiment of the resecting device with the jaw members engaging the tissue on one side of a human uterus wherein the procedure includes salpingoophorectomy.

If the surgical procedure is a LAVH or laparoscopic supracervical hysterectomy (with or without salpingoophorectomy), the resecting device 10 is placed adjacent to the uterus 81 as shown in FIGS. 14 and 15, and a grasping forcep 112 is also used. Such positioning allows for rapid electrosurgical treatment and/or division of all tissue on one side of the uterus 81 at once, including the infundibulopelvic ligament 82 or proper ovarian ligament 83, round ligament 84, fallopian tube 85, broad ligament 86 (shown in FIGS. 18-21), and lateral uterine vessels 87. The resecting device 10 also allows for easy and rapid removal of the ovaries 88 if the procedure includes salpingoophorectomy, wherein the infundibulopelvic ligament is divided, as shown in FIG. 17. The curvature of the jaw members 30, 32 also helps to mitigate incomplete or improper electrosurgical treatment of any portion of the uterine artery 95, which could lead to excessive bleeding. The curvature of the jaw members 30, 32 allows the user to approach the ascending branch of the uterine artery (the portion of the uterine artery 95 that is shown as following the outer wall of the uterus in FIGS. 14-18) in a more horizontal direction than devices of the prior art, which ensures that the ascending branch of the uterine artery is completely electrosurgically treated without damaging other portions of the uterine artery 95 or lateral uterine vessels 87. At the same time, the shape and dimension of the jaw members 30, 32 mitigates the possibility of damage to other surrounding tissues, such as the bladder 90, uterosacral ligament 91, ovaries 88 (depending on the procedure), rectum 96, and ureter 94.

After electrosurgical treatment and/or division of the proper tissue on the first side of the uterus 81 (which is the state shown in FIG. 18), the resecting device 10 is rotated 180 degrees and the same procedure is followed to electrosurgically treat and/or divide the tissue on the contra-lateral side of the uterus 81, thus freeing the upper portion of the uterus 81. FIG. 18 shows the resecting device positioned to treat the proper tissue on the contra-lateral side of the uterus 81 after the tissue on the first side has been treated. Once the upper portion of the uterus 81 has been freed, the uterus 81 is connected only at the uterocervical junction 93 (shown in FIG. 19).

At this point, the anterior vesicouterine fold 92 is opened by the jaw members 30, 32 and peeled off of the uterocervical junction 93. The user then deploys the wire loop 50 by positioning the wire loop switch 62 in the position corresponding to deployment of the wire loop 50 (or by manually rotating the wire spool 53 with the wire loop handle 58). As explained above, when the wire loop switch 62 is positioned to deploy the wire loop 50, an electric motor 51 engaged with the wire spool 53 and controlled by the wire loop switch 54 unwinds the wire on the wire spool 53 to extend the wire loop 50 until the wire loop 50 passes over the unattached upper portion of the uterus 81, as shown in FIG. 20. Once the wire loop 50 drapes over the uterus 81, the wire loop switch 54 is positioned so that the electric motor 51 and wire spool 53 are reversed; thereby retracting the wire loop 50 tightly against the cervix 89. When the wire loop 50 is securely in place around the uterus 81, the electrode selector 62 is set to the position that energizes the wire loop 50 by pressing the loop button 68, and the combination of the wire loop 50 retraction around the uterocervical junction 93 with energizing the wire loop 50, which is grounded through the contact plate 52 to form a bipolar electrosurgical delivery means, will hemostatically amputate the cervix in seconds. At that point, the completely unattached uterus 81 may be endoscopically removed with a morcellator, or through other appropriate means known to those skilled in the art.

Although many of the embodiments disclosed and pictured herein are specifically adapted to certain types of hysterectomies, the resecting device 10 is not limited by the specific surgical procedure for which it is adapted and/or used, but includes any endoscopic or laparoscopic procedure, as well as any open surgery. Therefore, any references to anatomical structures and/or tissues for which the resecting device 10 may be useful in electrosurgically treating, resecting, or dividing are meant to be illustrative examples only, and in no way limit the scope of the present invention. Accordingly, the resecting device 10 and the curvature of any portions thereof may vary within the scope of the present invention.

Although multiple embodiments of varying breadth have been pictured and disclosed herein, some including certain functionality absent in others, it should be noted that the present invention is not limited to the specific embodiments pictured and described herein. Instead the present invention is intended to apply to all similar apparatuses for applying electrosurgical energy to tissue wherein the application of electrosurgical energy is designed to result in dissection, removal, division, dessication, or other surgical functions any embodiment of the resecting device may be equipped to perform on specific tissues. Modifications and alterations from the described embodiments will occur to those skilled in the art without departure from the spirit and scope of the present invention.

What is claimed is: CLAIM1. A resecting device comprising:
a. a handle having a jaw trigger slidably engaged with said handle and mechanically engaged with a spring mechanism communicating a biasing force to said jaw trigger;
b. a fixed shaft portion having a first and a second end, wherein said fixed shaft portion first end is affixed to said housing, wherein said fixed shaft portion second end forms a first jaw member, and wherein said first jaw member has a tissue contact area;
c. a slidable shaft portion in communication with said spring mechanism and slidable relative to said fixed shaft portion, wherein said slidable shaft portion has a first and second end, wherein said slidable shaft portion first end is mechanically engaged with said spring mechanism, wherein said slidable shaft portion second end is mechanically engaged with a second jaw member so that said second jaw member and said first jaw member cooperate to form a set of cantilevered jaws, wherein said second jaw member has a tissue contact area oriented to face said tissue contact area of said first jaw member, wherein said tissue contact area of said first jaw member is biased away from said tissue contact area of said second jaw member via said spring mechanism, and wherein the distance between said tissue contact area of said first jaw member and said tissue contact area of said second jaw member is actuated by the position of said jaw trigger;
d. a source of electrosurgical energy adapted to connect to said jaw members such that said tissue contact areas of said jaw members are capable of conducting energy through tissues held therebetween. CLAIM2. The resecting device according to claim 1 wherein said handle is fashioned to be usable with either the left or right hand of a person without need to adjust the position of said resecting device. CLAIM3. The resecting device according to claim 1 wherein said first jaw member and said second jaw member are curved to emulate the periphery of the outer surface of a human uterus. CLAIM4. The resecting device according to claim 3 wherein said first and said second jaw members are of the same length, and wherein the length of said first and said second jaw members is selected to encompass substantially all the tissue on one side of the human uterus that must be electrosurgically treated in a hysterectomy. CLAIM5. The resecting device according to claim 3 wherein the distance between said tissue contact area of said first jaw member and said tissue contact area of said second jaw member is uniform across said jaw members at a particular position of said jaw trigger. CLAIM6. The resecting device according to claim 5 further comprising a blade, wherein said blade is slidably engaged with said shaft portions along a blade track passing through the interior of said shaft portions, said jaw members, and any linkage connecting said slidable shaft portion to said second jaw member, wherein said blade is mechanically engaged with a blade actuator, wherein said blade actuator is slidably engaged with said handle, and wherein the position of said blade with respect to said blade track is dependent on the position of said blade actuator. CLAIM7. The resecting device according to claim 6 wherein said blade track extends into a portion of said handle. CLAIM8. The resecting device according to claim 6 wherein said blade is extendable in a direction distal to said handle beyond the most distal portion, with respect to said handle, of said jaw members. CLAIM9. The resecting device according to claim 6 wherein said source of electrosurgical energy is further adapted to also connect to said blade so as to conduct energy through tissues in contact with said blade and either said first jaw member or said second jaw member. CLAIM10. The resecting device according to claim 9 wherein said handle further comprises an electrode selector, said electrode selector comprising:
a. an interior portion mounted within said handle, wherein said interior portion is in communication with each electrode of said resecting device that is capable of conducting electrosurgical energy, and wherein said first portion is in communication with said source of electrosurgical energy; and,
b. a exterior portion that is mounted outside of said handle, wherein said exterior portion provides a user interface for selecting the electrode to which said electrode selector routes electrosurgical energy. CLAIM11. The resecting device according to claim 10 further comprising a foot pedal in communication with said electrode selector and said source of electrosurgical energy, wherein said foot pedal functions as a switch between said electrode selector and said source of electrosurgical energy.

CLAIM 12. The resecting device according to claim 11 wherein said electrode selector allows the user of the tool to energize said tissue contact area on said first jaw member, said tissue contact area on said second member, or said blade, alone or in any combination thereof. CLAIM 13. The resecting device according to claim 1 further comprising:

a. a wire spool positioned within and rotatable with respect to said handle, wherein a wire capable of conducting electrosurgical energy is positioned around and engaged with a portion of said wire spool, and wherein a portion of said wire is orientated as a wire loop extending through an interior portion of said fixed shaft portion; and, b. a wire spool handle engaged with said wire spool, wherein said wire loop is deployable outwardly from said shaft through two wire apertures fashioned in the distal end of said fixed shaft portion via actuation of said wire spool handle in a first direction, and wherein said wire loop is retractable inwardly towards said shaft via actuation of said wire spool handle in a second direction.

CLAIM 14. The resecting device according to claim 13 further comprising an electric motor coupled to said wire spool, wherein said handle further comprises a wire loop switch in communication with said electric motor for actuating said electric motor. CLAIM 15. The resecting device according to claim 14 wherein said electric motor is rotatable in a first direction and a second direction opposite said first direction, and wherein said wire loop switch is operable to cause said electric motor to rotate in either of said directions or to remain stationary. CLAIM 16. The resecting device according to claim 13 wherein said fixed shaft portion further comprises a contact plate on said first jaw member oriented distal to said handle, wherein said source of electrosurgical energy is further adapted to also connect to said wire loop such that said loop is capable of conducting energy through tissues held between said wire loop and said contact plate. CLAIM 17. The resecting device according to claim 16 wherein said electrode selector is also in communication with said wire loop. CLAIM 18. The resecting device according to claim 11 or 17 wherein said electrode selector is fashioned to have a jaw button energizing said tissue contact areas of said jaw members, a blade button energizing said blade, and a loop button energizing said wire loop, wherein only one of said positions may be selected at one time. CLAIM 19. The resecting device according to claim 11 or 17 wherein said electrode selector is illuminated. CLAIM 20. The resecting device according to claim 17 wherein said electrode selector allows a user to energize said tissue contact area on said first jaw member, said tissue contact area on said second jaw member, said blade, or said wire loop alone or in any combination thereof. CLAIM 21. The resecting device according to claim 1 wherein the position of said jaw trigger is lockable. CLAIM 22. The resecting device according to claim 1 wherein said tissue contact area of said jaw members substantially extends the entire length of said jaw members. CLAIM 23. The resecting device according to claim 1 wherein at least a portion of said handle is further defined as being fashioned from a transparent or semi-transparent material. CLAIM 24. The resecting device according to claim 22 wherein said resecting device further comprises a light source within said handle that may illuminate either said electrode selector, said handle, or both. CLAIM 25. The resecting device according to claim 1 wherein at least a portion of said handle is further defined as being fashioned from a material that is self-illuminating after exposure to a light source. CLAIM 26. The resecting device according to claim 1 wherein a portion of the periphery of said slidable shaft portion and said fixed shaft portion are encompassed by a shaft sheath. CLAIM 27. The resecting device according to claim 1 wherein said shaft portions are comprises of an interior portion and an outer portion encompassing said interior portion. CLAIM 28. The resecting device according to claim 1 wherein said handle is further defined as being ambidextrous. CLAIM 29. The resecting device according to claim 1 wherein said handle is further defined as allowing 180 degree rotation of said resecting device to effectively treat both sides of an anatomical structure. CLAIM 30. A resecting device comprising:

a. a handle having a jaw trigger slidably engaged with said handle and mechanically attached to a spring mechanism communicating a biasing force to said jaw trigger;

b. a shaft affixed to said handle at a first end, said shaft having a second end engaged with a first jaw member and a second jaw member, said first and second jaw members each having a tissue contact area, wherein said tissue contact area of said second jaw member is oriented to face said tissue contact area of said first jaw member, wherein said first and second jaw members are mechanically engaged with said shaft so that said first and second jaw members cooperate to form a set of jaws wherein a distance between said tissue contact areas of said first and second jaw members is uniform along the length of said first and second jaw members, wherein said tissue contact area of said first jaw member is biased away from said tissue contact area of said second jaw member via said spring mechanism, and wherein the distance between said tissue contact area of said first jaw member and said tissue contact area of said second jaw member is actuated by the position of said jaw trigger, and c. a source of electrosurgical energy adapted to connect to said first and second jaw members such that said tissue contact areas of said first and second jaw members are capable of conducting energy through tissues held therebetween. CLAIM 31. A resecting device comprising:

a. a main body, said main body comprising:

i. a handle integrated into the structure of said main body;

ii. a jaw trigger slidably affixed to said main body at said handle;

iii. a spring mechanism in mechanical communication with said jaw trigger and located within said main body;

iv. an electrode selector having a switch, wherein said switch is mounted exterior said main body;

v. a blade actuator slidably engaged with said main body along a track in said main body;

b. a shaft affixed to said handle, said shaft comprising;

i. a first end affixed to said main body;

ii. a second end forming a first jaw member; and, iii. a blade track;

c. a second jaw member affixed to said shaft, wherein said second jaw member is affixed to said shaft in a manner such that said first jaw member and said second jaw member form cantilevered jaws, wherein said second jaw member is in mechanical communication with said jaw trigger and said spring mechanism, wherein said spring mechanism biases said second jaw member in a direction away from said first jaw member; and wherein the position of said second jaw member is actuated by said jaw trigger;

d. a selectively advanceable blade positioned within said shaft, wherein said blade is orientated towards said first and second jaw members, wherein said blade is in mechanical communication with and actuated by said blade actuator, and wherein said blade is actuated along said blade track; and, e. a source of electrosurgical energy adapted to connect to each jaw member at a tissue contact area such that said jaw members are capable of conducting energy through tissues held therebetween, wherein said source of electrosurgical energy is also adapted to connect to said blade such that said blade is capable of conducting energy through tissues located between said blade and said first or second jaw members, and wherein said electrode selector is capable of routing electrosurgical energy to said jaw members or said blade.

CLAIM32. The resecting device according to claim 31 wherein said first jaw member and said second jaw member employ a non-linear portion shaped to follow the contour of the outer wall of a human uterus.

CLAIM33. The resecting device according to claim 31 further comprising:

a. a wire spool positioned within and rotatable with respect to said handle, wherein a wire capable of conducting electrosurgical energy is positioned around and engaged with a portion of said wire spool, and wherein a portion of said wire is orientated as a wire loop extending through an interior portion of said shaft; and, b. a wire spool handle engaged with said wire spool, wherein said wire loop is deployable outwardly from said shaft through two wire apertures fashioned in the distal end of said shaft via actuation of said wire spool handle in a first direction, and wherein said wire loop is retractable inwardly towards said shaft via actuation of said wire spool handle in a second direction.

CLAIM34. The resecting device according to claim 33 further comprising an electric motor coupled to said wire spool, and wherein said handle further comprises a wire loop switch in communication with said electric motor for actuating said electric motor.

CLAIM35. The resecting device according to claim 34 wherein said electric motor is rotatable in a first direction and a second direction opposite said first direction, and wherein said wire loop switch is operable to cause said electric motor to rotate in either said direction or to remain stationary.

CLAIM36. The resecting device according to claim 33 wherein said shaft further comprises a contact plate on said first jaw member oriented distal to said handle, where said source of electrosurgical energy is further adapted to also connect to said wire loop such that said loop is capable of conducting energy through tissues held between said loop and said contact plate.

CLAIM37. A resecting device comprising:

a. a main body, said main body comprising:
  i. a handle integrated into the structure of said main body;
  ii. a jaw trigger slidably affixed to said main body at said handle;
  iii. a spring mechanism in mechanical communication with said jaw trigger and located within said main body;
  iv. an electrode selector having a switch, wherein said switch is mounted exterior said main body; and,
  v. a blade actuator slidably engaged with said main body along a blade actuator track;

b. a shaft affixed to said handle, said shaft comprising;
  i. a first end affixed to said main body;
  ii. a second end forming a first jaw member;
  iii. a contact plate orientated distally from said main body with respect to said first jaw member; and
  iv. a blade track;

c. a second jaw member affixed to said shaft, wherein said second jaw member is affixed to said shaft in a manner such that said first jaw member and said second jaw member form a set of cantilevered jaws, wherein said second jaw member is in mechanical communication with said jaw trigger and said spring mechanism, wherein said spring mechanism biases said second jaw member in a direction away from said first jaw member; and wherein the position of said second jaw member is actuated by said jaw trigger;

d. a selectively advanceable blade positioned within said shaft, wherein said blade is orientated towards said first and second jaw members, wherein said blade is in mechanical communication with and actuated by said blade actuator, and wherein said blade is actuated along said blade track;

e. a wire spool located within said main body, wherein said wire spool is mechanically engaged with a wire spool handle, wherein said wire spool handle is external said main body, wherein a portion of said wire spool is orientated as a wire loop extending through said shaft, wherein said wire loop is deployable outwardly from said shaft via actuation of said wire spool handle in a first direction and retractable inwardly to said shaft via actuation of said wire spool handle in a second direction, and wherein said wire loop may function as a wire loop resector; and f. a source of electrosurgical energy adapted to connect to each jaw member such that said jaw members are capable of conducting energy through tissues held therebetween, wherein said source of electrosurgical energy is also adapted to connect to said blade such that said blade is capable of conducting energy through tissues between said blade and said first jaw member or said second jaw member, and wherein said source of electrosurgical energy is also adapted to connect to said wire loop such that said wire loop is capable of conducting energy through tissues between said wire loop and said contact plate.

CLAIM38. An introducer sheath for facilitating the introduction of an instrument into a body opening of a patient comprising:

a. an introducer sheath body, wherein said introducer sheath body provides a path for passing said instrument therethrough, and wherein said introducer sheath body is fabricated of a flexible material;

b. a first end, wherein said first end is fashioned as an introducer sheath ring, and wherein said first end provides an opening into said introducer sheath body for said instrument;

c. a second end, wherein said second end is closed, wherein said second end is capable of being punctured with an appropriate surgical tool, and wherein said second end is fabricated of a flexible material; and, d. at least one group of perforations, wherein said group of perforations extend along at least one axial plane of said introducer sheath from said first end to said second end.

* * * * *